(12) United States Patent
Talley

(10) Patent No.: US 12,251,474 B2
(45) Date of Patent: Mar. 18, 2025

(54) PROCESS FOR LYOPHILIZED PHARMACEUTICAL FORMULATIONS OF A THERAPEUTIC PROTEIN

(71) Applicant: AMGEN INC., Thousand Oaks, CA (US)

(72) Inventor: Clea Talley, Camarillo, CA (US)

(73) Assignee: AMGEN INC., Thousand Oaks, CA (US)

( * ) Notice: Subject to any disclaimer, the term of this patent is extended or adjusted under 35 U.S.C. 154(b) by 861 days.

(21) Appl. No.: 16/652,667

(22) PCT Filed: Sep. 10, 2018

(86) PCT No.: PCT/US2018/050305
§ 371 (c)(1),
(2) Date: Mar. 31, 2020

(87) PCT Pub. No.: WO2019/055357
PCT Pub. Date: Mar. 21, 2019

(65) Prior Publication Data
US 2021/0369616 A1    Dec. 2, 2021

Related U.S. Application Data

(60) Provisional application No. 62/559,420, filed on Sep. 15, 2017.

(51) Int. Cl.
| | |
|---|---|
| A61K 9/19 | (2006.01) |
| A61K 38/19 | (2006.01) |
| A61K 39/395 | (2006.01) |
| A61K 47/02 | (2006.01) |
| A61K 47/10 | (2017.01) |
| A61K 47/18 | (2017.01) |
| A61K 47/22 | (2006.01) |
| A61K 47/26 | (2006.01) |
| A61K 47/40 | (2006.01) |
| C07K 14/52 | (2006.01) |
| C07K 16/28 | (2006.01) |
| C07K 16/32 | (2006.01) |

(52) U.S. Cl.
CPC .............. *A61K 9/19* (2013.01); *A61K 38/196* (2013.01); *A61K 39/395* (2013.01); *A61K 47/02* (2013.01); *A61K 47/10* (2013.01); *A61K 47/18* (2013.01); *A61K 47/183* (2013.01); *A61K 47/22* (2013.01); *A61K 47/26* (2013.01); *A61K 47/40* (2013.01); *C07K 14/524* (2013.01); *C07K 16/2809* (2013.01); *C07K 16/2848* (2013.01); *C07K 16/2863* (2013.01); *C07K 16/2878* (2013.01); *C07K 16/32* (2013.01)

(58) Field of Classification Search
CPC ...... A61K 9/19; A61K 38/196; A61K 39/395; A61K 47/02; A61K 47/10; A61K 47/18; A61K 47/183; A61K 47/22; A61K 47/26; A61K 47/40; A61K 38/00; A61K 2039/505; C07K 14/524; C07K 16/2809; C07K 16/2848; C07K 16/2863; C07K 16/2878; C07K 16/32

See application file for complete search history.

(56) References Cited

U.S. PATENT DOCUMENTS

| | | | |
|---|---|---|---|
| 5,730,969 A * | 3/1998 | Hora | A61K 47/6951 514/5.9 |
| 9,084,777 B2 | 7/2015 | Morichika et al. | |
| 2010/0144631 A1 | 6/2010 | Ron | |
| 2012/0028877 A1 | 2/2012 | Gokarn | |
| 2016/0000921 A1 | 1/2016 | Terracciano et al. | |
| 2016/0096791 A1 | 4/2016 | Nicewicz | |
| 2017/0112903 A1 * | 4/2017 | Gadgil | C07K 14/524 |

FOREIGN PATENT DOCUMENTS

| | | | |
|---|---|---|---|
| EP | 1977763 | A1 | 10/2008 |
| JP | 2005508992 | A | 4/2005 |
| JP | 2013500947 | A | 1/2013 |
| JP | 2014500879 | A | 1/2014 |
| WO | 198601533 | A1 | 3/1986 |
| WO | 198809344 | A1 | 12/1988 |
| WO | 199954440 | A1 | 10/1999 |
| WO | 2003041637 | A1 | 5/2003 |
| WO | 2004039337 | A1 | 5/2004 |

(Continued)

OTHER PUBLICATIONS

International Search Report for PCT/US2018/050305, mailed Jan. 18, 2019.

(Continued)

*Primary Examiner* — Robert A Wax
*Assistant Examiner* — Quanglong N Truong

(57) ABSTRACT

This invention concerns a process for making a lyophilized pharmaceutical formulation of a therapeutic protein, which comprises (a) providing a formulation of a bulk amount of the therapeutic protein, (b) measuring the concentration of the therapeutic protein in said bulk formulation, (c) adjusting the fill weight of the protein in said bulk formulation to achieve a fixed dose of the protein, and (d) lyophilizing the protein fill weight-adjusted formulation to achieve a final formulation in a container, wherein the product concentration post reconstitution with a fixed volume is within a predetermined acceptance range. The process is particularly suitable for formulations with low protein concentrations (e.g., 0.05 mg/mL to 20 mg/mL).

22 Claims, 8 Drawing Sheets
Specification includes a Sequence Listing.

(56) References Cited

FOREIGN PATENT DOCUMENTS

| WO | 2007074880 A1 | 7/2007 |
|---|---|---|
| WO | 2007124090 A2 | 11/2007 |
| WO | 2011012637 A2 | 2/2011 |
| WO | 2012066058 W | 5/2012 |
| WO | 201309679 A1 | 1/2013 |
| WO | 2013096791 W | 6/2013 |
| WO | 2015150968 A2 | 10/2015 |
| WO | 2017129585 A1 | 8/2017 |

OTHER PUBLICATIONS

AMG 330 [online] retrieved from: https://www.cancer.gov/about-cancer/treatment/clinical-trials/intervention/anti-cd33cd3- bite-antibody-amg-330; on Aug. 29, 2019; 1 page (Year: 2019).
AMG 701 [online] retrieved from: https://www.cancer.gov/publications/dictionaries/cancer-drug/def/792377; on Aug. 29, 2019; 2 pages ( Year: 2019).
Anzsrs Poster Presentations, abstracts AP-001 to AP-013, pp. 11-17, Mar. 15, 2017.
Arakawa et al., "Protein-Solvent Interactions in Pharmaceutical Formulations", Pharm. Res., vol. 8 (3), pp. 285-291 (1991).
Assessment report blinatumomab, 2015.
Ausubel et al. (Eds.), Current Protocols in Molecular Biology, vol. 1, Suppl. 47, John Wiley & Sons Inc., Table of Contents (1992).
Blinatumomab [online] retrieved from: http://chemocare.com/chemotherapy/drug-info/blinatumomab.aspx; on Aug. 29, 2019; 6 pages ( Year: 2019).
Brühl, H. et al., "Depletion of CCR5-Expressing Cells with Bispecific Antibodies and Chemokine Toxins: A New Strategy in the Treatment of Chronic Inflammatory Diseases and HIV," J Immunol., 166:2420-2426 (2001).
Cacace et al., "The Hofmeister series: salt and solvent effects on interfacial phenomena," Q Rev Biophys., vol. 30(3), pp. 241-277 (1997).
Cameron, P., Ed., Good Pharmaceutical Freeze-Drying Practice, Interpharm Press, Inc., Buffalo Grove, IL (1997) (Table of Contents Only).
Carpenter et al., "Interactions of stabilizing additives with proteins during freeze-thawing and freeze-drying," Developments in Biological Standardization 74: 225-238 (1992).
Chang, B. S. et al., "Surface-Induced Denaturation of Proteins during Freezing and its Inhibition by Surfactants," J. Pharm. Sci., 85(12):1325-1330 (1996).
Chapter 14: Sterile Filtration, Filling, and Lyophilization of Product, in Introduction to Biomanufacturing, Northeast Biomanufacturina Center & Collaborative (NBC2 ); 2016, oaae 1-85.
Cheadle et al., "Cloning and Expression of the Variable Regions of Mouse Myeloma Protein MOPC315 in E. coli: Recovery of Active Fv Fragments", Molec. Immunol., vol. 29 (1), pp. 21-30 (1992).
Chen, B. et al., "Influence of calcium ions on the structure and stability of recombinant human deoxyribonuclease I in the aqueous and lyophilized states," J Pharm Sci., 88(4):477 482 (1999).
Chevalier et al., "Maillard glycation of beta-lactoglobulin induces conformation changes," Nahrung/Food, vol. 46 (2), pp. 58-63 (2002).
Cleland, J. L. et al., "The development of stable protein formulations: a close look at protein aggregation, deamidation, and oxidation," Critical Reviews in Therapeutic Drug Carrier Systems, 10(4):307-377 (1993).
Dall'Acqua, W. et al., "Contributions of Domain Interface Residues to the Stability of Antibody CH3 Domain Homodimers," Biochem., 37(26):9266-9273 (1998).
Derrick et al., "Effect of metal cations on the conformation and inactivation of recombinant human factor VIII," Journal of Pharmaceutical Sciences, vol. 93 (10), pp. 2549-2557 (2004).
Fatouros et al., "Recombinant Factor VIII SQ—Influence of Oxygen, Metal Ions, Ph and Ionic Strength on Its Stability in Aqueous Solution", International Journal of Pharmaceutics, vol. 155 (1), pp. 121-131 (Sep. 1997).

Harlow and Lane, Antibodies: A Laboratory Manual, Cold Spring Harbor Laboratory, USA, Table of Contents (1988).
Holleman-Wiberg, Lehrbuch der Anorganischen Chemie, edited by Nils Wiberg, edi. 91.-100., Walter de Gruvter, Berlin, New York, 1985, p. 30.
Holliger, Philipp et al., Proceedings of the National Academy of Sciences of the USA, 90(14):6444-6448 (1993).
Humeny et al., "Qualitative determination of specific protein glycation products by matrix-assisted laser desorption/ionization mass spectrometry Peptide mapping", J Agric Food Chem., vol. 50 (7), pp. 2153-2160 (2002).
Huston et al., "Protein engineering of antibody binding sites: recovery of specific activity in an anti-digoxin single-chain Fv analogue produced in Escherichia coli", Proc. Natl. Acad. Sci. USA, vol. 85 (16), pp. 5879-5883 (1988).
Jameel, F., Hershenson, S., Khan, M.A., & Martin-Moe, S. (Eds.). (2015). Chapter 13 Application of QbD Elements in the Development and Scale-up of Commercial Filling Process. In: Quality by Design for Biopharmaceutical Drug Product Development. Springer. https://doi.org/10.1007/978-1-4939-2316-8.
Kamerzell, T. J. et al., "Protein-excipient interactions: Mechanisms and biophysical characterization applied to protein formulation development," Advanced Drug Delivery Rev., 63(13):1118-1159 (2011).
Kanojia G. et al. The Production of a Stable Infliximab Powder: The Evaluation of Spray and Freeze-Drying for Production. PLoS One. Oct. 5, 2016;11 (1O):e0163109. doi:10.1371/journal.pone.0163109. PMID: 27706175; PMCID: PMC5051734.
Kappelgaard et al., "Liquid growth hormone: preservatives and buffers", Horm Res., vol. 62 (Suppl. 3), pp. 98-103 (2004).
Kautz, C. F. and Robinson, A. L., "The Hydrolysis of Sucrose by Hydrochloric Acid in the Presence of Alkali and Alkaline Earth Chlorides," JACS, 50(4):1022-1030 (1928).
Kipriyanov, S. M. et al., "Bispecific tandem diabody for tumor therapy with improved antigen binding and pharmacokinetics," J. Mol. Biol., 293(1):41-56 (1999).
Kufer, P. et al., "Construction and biological activity of a recombinant bispecific single-chain antibody designed for therapy of minimal residual colorectal cancer," Cancer Immunol., Immunother., 45(3-4):193-197 (1997).
Kufer, P., et al., "A revival of bispecific antibodies," Trends in Biotechnology, 22(5):238 244 (2004).
Lee et al., "Thermal Stability of Proteins in the Presence of Poly(ethylene glycols)", Biochemistry, vol. 26 (24), pp. 7813-7819 (1987).
Liu, J. et al., "Reversible self-association increases the viscosity of a concentrated monoclonal antibody in aqueous solution," J. Pharm Sci., 94(9):1928-1940 (2005.
Löffler et al., "A recombinant bispecific single-chain antibody, CD19×CD3, induces rapid and high lymphoma-directed cytotoxicity by unstimulated T lymphocytes", Blood, vol. 95 (6), pp. 2098-2103 (2000).
Mack, M. et al., "A small bispecific antibody construct expressed as a functional single-chain molecule with high tumor cell cytotoxicity," PNAS, 92(15):7021-7025 (1995).
Mack, M. et al., "Biologic properties of a bispecific single-chain antibody directed against 17-1A (EpCAM) and CD3: tumor cell-dependent T cell stimulation and cytotoxic activity," J. Immunol., 158(8):3965-3970 (1997).
Minogue et al., "Bacteriostatic saline containing benzyl alcohol decreases the pain associated with the injection of propofol", Anesth Analg., vol. 100 (3), pp. 683-686 (2005).
Morrison et al., "Chimeric human antibody molecules: mouse antigen-binding domains with human constant region domains", Proc. Natl. Acad. Sci. USA, vol. 81 (21), pp. 6851-6855 (1984).
Nplate TM Romiplostim Highlights of Prescribing Information ([online] retrieved from: https://www.accessdata.fda.gov/drugsatfdadocs/label/2009/125268s00261b1.pdf; Aug. 1, 2008; 11 pages). (Year: 2008).
Patro S.Y., Freund E. and Chang B. S., Protein formulation and fill-finisch operations, Biotechnology Annual Review, 2002.
Peterson, A., Chapter 6: Viral Processing—Accumulating, Conveying, Filling and Stoppering the Most Common Parenteral Container,

(56) References Cited

OTHER PUBLICATIONS

Chapter 7: Checkweighing Fill Weight of Parenteral Product is the Hart of Process Quality, Chapter 8: Filling Methods as they Apply to Parenteral Product Quality and Biopharmaceutical Microdosing, in Practical Aseptic Processing: Fill and Finish; edited by Lysfjord, J.; Parental Druq Association, Bethesda, MD, USA; 2009, pp. 105-150.

Pikal, M.J., "Freeze-drying of proteins. Part II. Formulation selection," Biopharm., 3(9): 26-30 (1990).

Powell et al., "Compendium of excipients for parenteral formulations", PDA J Pharm Sci Technol., vol. 52 (5), pp. 238-311 (1998).

Raag and Whitlow, "Single-chain Fvs", FASEB J., vol. 9, pp. 73-80 (1995).

Randolph and Jones, "Surfactant-protein interactions", Rational Design of Stable Protein Formulations, Eds. Carpenter and Manning, Kluwer Academic, Plenum Publishers, New York, pp. 159-175 (2002).

Remmele et al., "Interleukin-1 receptor (IL-1R) liquid formulation development using differential scanning calorimetry", Pharm Res., vol. 15 (2), pp. 200-208 (1998).

Remmele et al., "Minimization of Recombinant Human Flt3 Ligand Aggregation at the Tm Plateau: A Matter of Thermal Reversibility", Biochemistry, vol. 38 (16), pp. 5241-5247 (1999).

Communication of a Notice of Opposition for EP 3 681 483 B1 mailed Feb. 22, 2023.

Label romiplostim; Dec. 2011.

Notice of Opposition to a European Patent by JG Oppositions Limited for EP 3 681 483 B1 filed Feb. 17, 2023.

Notice of Opposition to a European Patent by Oetke, Ms. Comelia for EP 3 681 483 B1 filed Feb. 20, 2023.

Notice of Opposition to a European Patent by Withers & Rogers LLP for EP 3 681 483 B1 filed Feb. 20, 2023.

Rompps Chemie-Lexikon, 7th edi., 1973, Franckh'sche Verlagshandlung, Stuttgart, p. 833.

Roy et al., "Effects of Benzyl Alcohol on Aggregation of Recombinant Human Interleukin-1-Receptor Antagonist in Reconstituted Lyophilized Formulations", Journal of Pharmaceutical Sciences, vol. 94 (2), pp. 382-396 (2005).

Sambrook and Russell, "Molecular Cloning: A Laboratory Manual", 3rd Ed., Cold Spring Harbor Laboratory Press, New York, vol. 1, Table of Contents (2001).

Screenshot Chapter 14 opening from webpage shown in D4c {http://web.archive.org/web/20161106232458/http://biomanufacturing.org/uploads/files/340852170209494547-chapter-14.pdf) from Nov. 6, 2016.

Screenshot of Google search results, Feb. 13, 2023.

Screenshot of the website of the Official Journal of the Asian Pacific Society of Respirology "Respirology" showina the ANZSRS Poster Presentation with the publication date of Mar. 15, 2017.

Screenshot of web page from May 22, 2017; snapshot 19:47:40 (http://web.archive.org/web/20170522194 7 40/https://piomanufacturing .org/curriculumresources/textbooks-manuals/introduction-to-biomanufacturing).

Screenshot Waybackmachine (http://web.archive.org/web/20230000000000*/ https://biomanufacturing.org/curriculum-resources/textbooks-manuals/introduction-tobiomanufacturing): result for https://biomanufacturing.org/curriculum-resources/textbooksmanuals/introduction-to-biomanufacturing. first saved May 22, 2017.

Songsivilai and Lachmann, "Bispecific antibody: a tool for diagnosis and treatment of disease", Clin. Exp. Immunol., vol. 79 (3), pp. 315-321 (1990).

Table of chapters of contents of Introduction to Biomanufacturing, Northeast Biomanufacturing Center & Collaborative (NBC2) containing Chapter 14 (04) (https://biomanufacturing.org/curriculum-resources/textbooks-manuals/introduction-tobiomanufacturina).

Takeda et al., "Construction of chimaeric processed immunoglobulin genes containing mouse variable and human constant region sequences", Nature, vol. 314, pp. 452-454 (1985).

Trastuzumab [online] retrieved from: http://chemocare.com/chemotherapy/drug-info/Trastuzumab.aspx; on Aug. 29, 2019; 6 pages. (Year: 2019).

United States Pharmacopeia (USP), sec. 1151: Pharmaceutical Dosage Forms, 2012.

EP 3 681 483 Response to Notices of Opposition (Sep. 19, 2023).

Optek Technology, Inc. "Product information Control 4000 Photometric Analyzers Control 8000 Universal Analyzers" [retrieved from the internet May 13, 2024] <URL:https://web.archive.org/web/20130410145631/http://www.pryde.com.au/Data_Sheets/Analytical_65/Converters/C4004-C8000-Datasheet.pdf> (archived by web. archive. org on Apr. 10, 2013) [2] Category.

Communication from the EP Patent office for EP127476-HV dated Jan. 18, 2024 enclosing a letter from the Opponent.

Communication from the EP Patent office for EP127476-HV dated Mar. 3, 2024 enclosing a letter from the Opponent.

Cornelia Oetke's Observations in preparation for Oral Proceedings dated Nov. 18, 2024 for EP 3681483.

JG Oppositions Response to Oral Proceeding dated Nov. 20, 2024 for EP 3681483.

Patent Proprietor's Response to the summons to oral proceedings and additional submission of Opponent 3 for EP 3681483 dated Nov. 20, 2024.

* cited by examiner

- Likely Fill Target Error
- Stepped-in DP Concentration Spec
- Osmo Spec
- IPC/Alert Limit Operational Range

FIG. 8

| Cosolute | | | Stabilization scales | |
|---|---|---|---|---|
| Anion | Cation | Other | | |
| F⁻ | (CH₃)₄N⁺ | Glycerol/Sorbitol | Stabilizing (salting-out) | Kosmotropic |
| PO₄³⁻ | (CH₃)₃NH⁺ | Sucrose/Trehalose | | |
| SO₄²⁻ | NH₄⁺ | TMAO | | |
| CHCOO⁻ | K⁺ | | ↕ | ↕ |
| Cl⁻ | Na⁺ | | | |
| Br⁻ | Cs⁺ | | | |
| I⁻ | Li⁺ | | | |
| | Mg²⁺ | Guanidine | | |
| | Ca²⁺ | Arginine | | |
| | Ba²⁺ | Urea | Destabilizing (salting-in) | Chaotropic |

SEQUENCE LISTING

```
<160> NUMBER OF SEQ ID NOS: 1

<210> SEQ ID NO 1
<211> LENGTH: 5
<212> TYPE: PRT
<213> ORGANISM: ARTIFICIAL SEQUENCE
<220> FEATURE:
<223> OTHER INFORMATION: Peptide linker

<400> SEQUENCE: 1

Gly Gly Gly Gly Ser
1               5
```

PROCESS FOR LYOPHILIZED PHARMACEUTICAL FORMULATIONS OF A THERAPEUTIC PROTEIN

CROSS-REFERENCE TO RELATED APPLICATIONS

This application is a national stage application under 35 U.S.C. § 371 of International Application No. International Application No. PCT/US2018/050305, having an international filing date of 10 Sep. 2018, which claims the benefit of U.S. Provisional Application No. 62/559,420, filed on 15 Sep. 2017, each of which is hereby incorporated by reference in their entirety for all purposes.

FIELD OF THE INVENTION

This invention relates to biopharmaceuticals, particularly to therapeutic proteins, methods of use thereof, pharmaceutical formulations thereof, and processes of making pharmaceutical formulations. In particular, this invention relates to processes for making lyophilized pharmaceutical formulations.

BACKGROUND OF THE INVENTION

In the past ten years, advances in technology have made it possible to produce a variety of active molecules for pharmaceutical applications. As the nature of understanding of mechanisms of biological action progresses, these molecules can be designed for certain attributes, where small amounts of product can be efficacious.

Because these molecules can be larger and/or more complex than traditional organic and inorganic drugs (i.e. possessing multiple functional groups in addition to complex three-dimensional structures), the formulation of such products poses special problems. For a product to remain biologically active, a formulation must preserve intact the conformational integrity of at least a core sequence of the protein's amino acids while at the same time protecting the protein's multiple functional groups from degradation. Degradation pathways for proteins can involve chemical instability (i.e. any process which involves modification of the protein by bond formation or cleavage resulting in a new chemical entity) or physical instability (i.e. changes in the higher order structure of the protein). Chemical instability can result from deamidation, racemization, hydrolysis, oxidation, beta elimination or disulfide exchange. Physical instability can result from denaturation, aggregation, precipitation or adsorption, for example. The three most common protein degradation pathways are protein aggregation, deamidation and oxidation. Cleland et al. (1993), Critical Reviews in Therapeutic Drug Carrier Systems 10 (4): 307-377.

These designed molecules due to their synthetic nature are prevalently lyophilized (freeze dried) as the presentation can provide improved shelf stability. Freeze-drying is a commonly employed technique for preserving proteins which serves to remove water from the protein preparation of interest. Freeze-drying, or lyophilization, is a process by which the material to be dried is first frozen and then the ice or frozen solvent is removed by sublimation in a vacuum environment. An excipient may be included in pre-lyophilized formulations to enhance stability during the freeze-drying process and/or to improve stability of the lyophilized product upon storage. Pikal, M. (1990), Biopharm. 3 (9) 26-30 and Arakawa et al. (1991), Pharm. Res. 8 (3): 285-291.

A designed molecule with specific biological targets and the resulting dosage requirements for product poses new problems for the manufacturing process. The current art involves a simple process where product is formulated to a targeted concentration and then filled into containers at a set volume.

SUMMARY OF THE INVENTION

This invention is directed to a process to generate lyophilized drug product. In particular, it relates to the formulation, fill, and assurance of the required amount of product present post-reconstitution with a fixed volume of diluent of a lyophilized product for use.

Provided in accordance with the present invention is a process for making a lyophilized pharmaceutical formulation of a therapeutic protein, which comprises:

(a) providing a formulation of a bulk amount of the therapeutic protein, (b) measuring the concentration of the therapeutic protein in said bulk formulation, (c) adjusting the fill weight of the protein in said bulk formulation to achieve a fixed dose of the protein, and (d) lyophilizing the protein fill weight-adjusted formulation to achieve a final formulation in a container.

wherein the product concentration post reconstitution with a fixed volume is within a predetermined acceptance range In the foregoing process, the protein concentration in the final formulation is preferred to be less than or equal to about 20 or 25 mg/mL, with about 0.5 mg/mL, about 0.05 mg/mL about 18 mg/mL about 20 mg/mL and about 21 mg/mL most preferred. Preferred therapeutic proteins in the processes of this invention are romiplostim, blinatumomab, infliximab, trastuzumab, AMG 701, and AMG 330. AMG 701 and AMG 330 are bispecific single chain antibody constructs and other bispecific single chain antibody constructs (e.g., bispecific T cell engagers) are preferred therapeutic proteins in the processes of the invention. Preferred pharmaceutical excipients present in the formulation comprise sugars, with trehalose, sucrose and a hydrate of either most preferred. Preferred pharmaceutical excipients also comprise buffers, with histidine, citric acid monohydrate, sodium phosphate, potassium phosphate, and glutamic acid preferred. Preferred excipients further comprise surfactants, with polysorbate 20 and polysorbate 80 most preferred. Preferred excipients and therapeutic proteins used in accordance with the processes of this invention appear in Table 1, with about the preferred concentrations of each listed below each protein and excipient.

TABLE 1

Preferred Formulation Components

| Protein | Sugar | Buffer | Bulking agent/Solubilizing agent | Surfactant | pH |
|---|---|---|---|---|---|
| romiplostim 0.5 mg/mL | Sucrose 2% w/v | Histidine 10 mM | Mannitol 4% w/v | Polysorbate 20 0.004% w/v | 5.0 |
| blinatumomab 55 mcg/mL | Trehalose 15% w/v | Citric acid monohydrate 25 mM; L-lysine hydrochloride 200 mM | — | Polysorbate 80 0.1% w/v | 7.0 |
| infliximab 20 ± 1.5 mg/mL | Sucrose 10% w/v | Sodium phosphate 10 mM | — | Polysorbate 80 0.01% w/v | 7.2 |
| trastuzumab 21 mg/mL | á,á-trehalose dehydrate 19.1 mg/mL | Histidine 0.303 mg/mL; L-histidine hydrochloride monohydrate 0.470 mg/mL | — | Polysorbate 20 0.0840 mg/mL | 6.1 |
| AMG 701 1 mg/mL | Sucrose 9% w/v | L-Glutamic acid 10 mM | — | Polysorbate 80 0.010% w/v | 4.2 |
| AMG 330 0.5 mg/mL | Sucrose 8% w/v | Potassium phosphate 10 mM | SBE-CD 1% w/v | Polysorbate 80 0.010% w/v | 6.1 |

Further in accordance with the present invention, the formulation may comprise other excipients as described hereinbelow.

BRIEF DESCRIPTION OF THE DRAWINGS

FIG. 8 shows The Hofmeister series of salts.

DETAILED DESCRIPTION OF THE INVENTION

Definition of Terms

Figure 1:
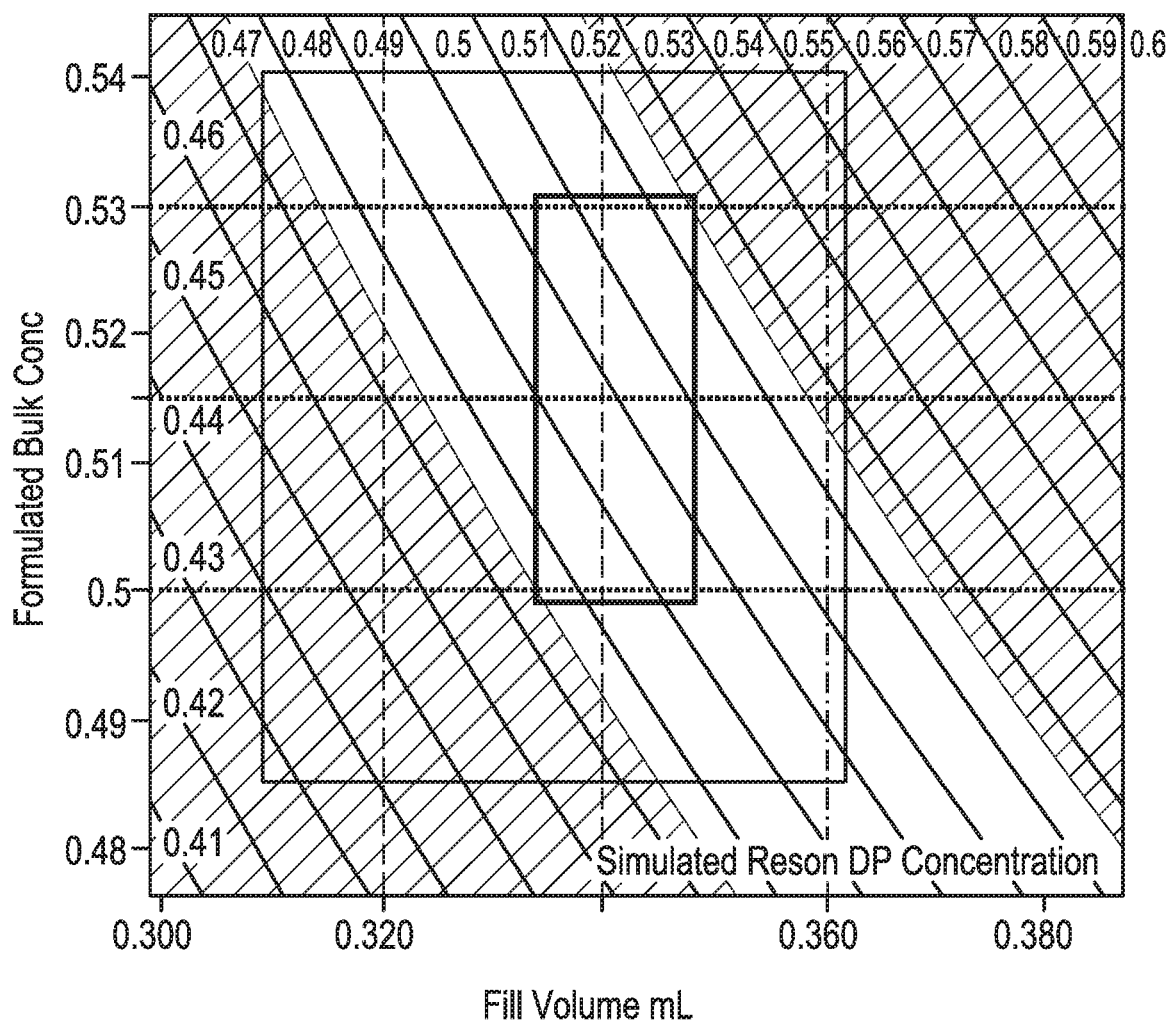
FIG. 1 is a response surface map showing an example design space for a low dose product in which formulation and fill weight would follow a typical control strategy. The gray space represents wherein method/reconstitution variability would have a greater than 50% probability of having a failed protein concentration result. The large square shows the current operating range for formulation development. The smaller rectangle shows an effective operating range.

In the description that follows, a number of terms are used extensively. The following definitions are provided to facilitate understanding of the invention.

Unless otherwise specified, "a", "an", "the", and "at least one" are used interchangeably and mean one or more than one. In addition, unless otherwise required by context, singular terms shall include pluralities and plural terms shall include the singular.

As used herein, a "pharmaceutical formulation" or a "formulation" is a sterile composition of (i) a pharmaceutically active drug, such as a biologically active protein, that is suitable for parenteral administration (including but not limited to intravenous, intramuscular, subcutaneous, aerosolized, intrapulmonary, intranasal and intrathecal administration) to a patient in need thereof and (ii) one or more pharmaceutically acceptable excipients, diluents, and other additives deemed safe by the Federal Drug Administration or other foreign national authorities. Pharmaceutical formulations include liquid (e.g., aqueous) solutions that may be directly administered, and lyophilized powders that may be reconstituted into solutions by adding a diluent before administration. The term "pharmaceutical formulation" specifically excludes, however, compositions for topical administration to patients, compositions for oral ingestion, and compositions for parenteral feeding.

"Shelf life", as used herein, means that the storage period during which an active ingredient (e.g., an antibody) in a pharmaceutical formulation has minimal degradation (e.g., not more than about 5% to 10% degradation) when the pharmaceutical formulation is stored under specified storage conditions (e.g., 2-8° C.). Techniques for assessing degradation vary depending on the identity of the protein in the pharmaceutical formulation. Exemplary techniques include size-exclusion chromatography (SEC)-HPLC to detect, for example, aggregation; reverse phase (RP)-HPLC to detect, for example, protein fragmentation; ion exchange-HPLC to detect, for example, changes in the charge of the protein; and mass spectrometry, fluorescence spectroscopy, circular dichroism (CD) spectroscopy, Fourier transform infrared spectroscopy (FT-IR), and Raman spectroscopy to detect protein conformational changes. All of these techniques can be used singly or in combination to assess the degradation of the protein in the pharmaceutical formulation and determine the shelf life of that formulation. The pharmaceutical formulations of the present invention preferably exhibit not more than about 5 to 10% increases in degradation (e.g., fragmentation, aggregation or unfolding) over two years when stored at 2-8° C.

As used herein, "stable" formulations of biologically active proteins are formulations that exhibit either (i) reduced aggregation and/or reduced loss of biological activity of at least 20% upon storage at 2-8° C. for at least 2 years compared with a control formula sample, or (ii) reduced aggregation and/or reduced loss of biological activity under conditions of thermal stress (e.g. 25° C. for 1 week to 12 weeks; 40° C. for 1 to 12 weeks; 52° C. for 7-8 days, etc.). In an embodiment, a formulation is considered stable when the protein in the formulation retains its physical stability, chemical stability and/or biological activity.

A protein may be said to "retain its physical stability" in a formulation if, for example, it shows no signs of aggregation, precipitation and/or denaturation upon visual examination of color and/or clarity, or as measured by UV light scattering or by size exclusion chromatography (SEC) or electrophoresis, such as with reference to turbidity or aggregate formation.

A protein may be said to "retain its chemical stability" in a formulation if, for example, the chemical stability at a given time is such that no new chemical entity results from modification of the protein by bond formation or cleavage. In a further embodiment, chemical stability can be assessed by detecting and quantifying chemically altered forms of the protein. Chemical alteration may involve, for example, size modification (e.g., clipping), which can be evaluated using size exclusion chromatography, SDS-PAGE and/or matrix-assisted laser desorption ionization/time-of-flight mass spectrometry (MALDI/TOF MS). Other types of chemical alteration include, for example, charge alteration (e.g., resulting from deamidation), which can be evaluated by ion-exchange chromatography. Oxidation is another commonly seen chemical modification.

A protein may be said to "retain its biological activity" in a pharmaceutical formulation relative to unmodified protein if, for example, the percentage of biological activity of the formulated protein (e.g., an antibody) as determined by an assay (e.g., an antigen binding assay) compared to the control solution is between either about 50% and about 200%, about 60% and about 170%, about 70% and about 150%, about 80% and about 125%, or about 90% and about 110%. In a further embodiment, a protein may be said to "retain its biological activity" in a pharmaceutical formulation, if, for example, without limitation, the biological activity of the protein at a given time is at least 1%, 5%, 10%, 15%, 20%, 25%, 30%, 35%, 40%, 45%, 50%, 55%, 60%, 65%, 70%, 75%, 80%, 85%, 90%, 95% or 100%.

As used herein, the terms "comprising" and "comprises" are intended to mean that the formulations and methods include the listed elements but do not exclude other unlisted elements. The terms "consisting essentially of" and "consists essentially of," when used to define formulations and methods include the listed elements, exclude unlisted elements that alter the basic nature of the formulation and/or method, but do not exclude other unlisted elements. So a formulation consisting essentially of elements defined herein would not exclude trace amounts of other elements, such as contaminants from any isolation and purification methods or pharmaceutically acceptable carriers (e.g., phosphate buffered saline), preservatives, and the like, but would exclude, for example, additional unspecified amino acids. The terms "consisting of" and "consists of" when used to define formulations and methods exclude more than trace elements of other ingredients and substantial method steps for administering the compositions described herein. Embodiments defined by each of these transition terms are within the scope of this disclosure and the inventions embodied herein.

The term "isolated" as used herein refers to a protein (e.g., an antibody) that has been identified and separated and/or recovered from a component of its natural environment. Contaminant components of its natural environment are materials which would interfere with diagnostic or therapeutic uses for the protein, and may include enzymes, hormones, and other proteinaceous or nonproteinaceous solutes. In preferred embodiments, the protein will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated protein includes the protein in situ within recombinant cells since at least one component of the protein's natural environment will not be present. Ordinarily, however, isolated protein will be prepared by at least one purification step.

The invention concerns processes for pharmaceutical formulations of therapeutic proteins such as antibodies. "Antibodies" (Abs) and the synonym "immunoglobulins" (Igs)

are glycoproteins having the same structural characteristics. While antibodies exhibit binding specificity to a specific antigen, immunoglobulins include both antibodies and other antibody-like molecules that lack antigen specificity. Polypeptides of the latter kind are, for example, produced at low levels by the lymph system and at increased levels by myelomas. Thus, as used herein, the term "antibody" or "antibody peptide(s)" refers to an intact antibody, an antibody derivative, an antibody analog, a genetically altered antibody, an antibody having a detectable label, an antibody that competes for specific binding with an antibody disclosed in this specification, or an antigen-binding fragment (e.g., Fab, Fab', F(ab')$_2$, Fv, single domain antibody) thereof that competes with the intact antibody for specific binding and includes chimeric, humanized, fully human, and bispecific antibodies. In certain embodiments, antigen-binding fragments are produced, for example, by recombinant DNA techniques. In additional embodiments, antigen-binding fragments are produced by enzymatic or chemical cleavage of intact antibodies. Antigen-binding fragments include, but are not limited to, Fab, Fab', F (ab) 2, F(ab')$_2$, Fv, and single-chain antibodies.

The term "intact antibodies" as used herein refers to antibodies comprising two heavy chains and two light chains. This term thus includes without limitation fully human antibodies, genetically altered antibodies, bispecific antibodies, and antibody derivatives provided such antibodies comprised two heavy chains and two light chains.

The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

The monoclonal antibodies and antibody constructs formulated in accordance with the present invention specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is/are identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al. (1984), Proc. Natl. Acad. Sci. USA, 81:6851-6855). Chimeric antibodies of interest herein include "primitized" antibodies comprising variable domain antigen-binding sequences derived from a non-human primate (e.g., Old World Monkey, Ape, etc.) and human constant region sequences. A variety of approaches for making chimeric antibodies have been described. See e.g., Morrison et al. (1985), Proc. Natl. Acad. Sci. U.S.A. 81:6851; Takeda et al. (1985), Nature 314:452, Cabilly et al., U.S. Pat. No. 4,816,567; Boss et al., U.S. Pat. No. 4,816,397; Tanaguchi et al., EP 0171496; EP 0173494; and GB 2177096.

The monoclonal antibodies and antibody constructs formulated in accordance with the present invention specifically include antibodies referred to as "human" or "fully human." The terms "human antibody" and "fully human antibody" each refer to an antibody that has an amino acid sequence of a human immunoglobulin, including antibodies isolated from human immunoglobulin libraries or from animals transgenic for one or more human immunoglobulins and that do not express endogenous immunoglobulins; for example, Xenomouse® antibodies and antibodies as described by Kucherlapati et al. in U.S. Pat. No. 5,939,598.

The term "genetically altered antibodies" means antibodies wherein the amino acid sequence has been varied from that of a native antibody. Because of the relevance of recombinant DNA techniques in the generation of antibodies, one need not be confined to the sequences of amino acids found in natural antibodies; antibodies can be redesigned to obtain desired characteristics. The possible variations are many and range from changes to just one or a few amino acids to complete redesign of, for example, the variable and/or constant region. Changes in the constant region will, in general, be made in order to improve or alter characteristics, such as complement fixation, interaction with membranes and other effector functions, as well as manufacturability and viscosity. Changes in the variable region will be made in order to improve the antigen binding characteristics.

A "Fab fragment" is comprised of one light chain and the $C_{H1}$ and variable regions of one heavy chain. The heavy chain of a Fab molecule cannot form a disulfide bond with another heavy chain molecule.

A "Fab' fragment" contains one light chain and one heavy chain that contains more of the constant region, between the $C_{H1}$ and $C_{H2}$ domains, such that an interchain disulfide bond can be formed between two heavy chains to form a F(ab')$_2$ molecule.

A "F(ab')$_2$ fragment" contains two light chains and two heavy chains containing a portion of the constant region between the $C_{H1}$ and $C_{H2}$ domains, such that an interchain disulfide bond is formed between two heavy chains.

The terms "Fv fragment" and "single chain antibody" refer to polypeptides containing antibody variable regions from both heavy and light chains but lacking constant regions. Like a whole antibody, it is able to bind selectively to a specific antigen. With a molecular weight of only about 25 kDa, Fv fragments are much smaller than common antibodies (150-160 kD) which are composed of two heavy protein chains and two light chains, and even smaller than Fab fragments (about 50 kDa, one light chain and half a heavy chain).

A "single domain antibody" is an antibody fragment consisting of a single domain Fv unit, e.g., $V_H$ or $V_L$. Like a whole antibody, it is able to bind selectively to a specific antigen. With a molecular weight of only 12-15 kDa, single-domain antibodies are much smaller than common antibodies (150-160 kDa) which are composed of two heavy protein chains and two light chains, and even smaller than Fab fragments (.about.50 kDa, one light chain and half a heavy chain) and single-chain variable fragments (.about.25 kDa, two variable domains, one from a light and one from a heavy chain). The first single-domain antibodies were engineered from heavy-chain antibodies found in camelids. Although most research into single-domain antibodies is currently based on heavy chain variable domains, light chain variable domains and nanobodies derived from light chains have also been shown to bind specifically to target epitopes.

The term "bispecific" as used herein refers to an antibody construct which is "at least bispecific", i.e., it comprises at least a first binding domain and a second binding domain, wherein the first binding domain binds to one antigen or target (e.g., CD3), and the second binding domain binds to another antigen or target (e.g., BCMA; e.g., CD 33). Accordingly, antibody constructs according to the invention comprise specificities for at least two different antigens or targets. The term "bispecific antibody construct" of the invention also encompasses multispecific antibody constructs such as trispecific antibody constructs, the latter ones including three binding domains, or constructs having more than three (e.g. four, five . . . ) specificities.

Given that the antibody constructs according to the invention are (at least) bispecific, they do not occur naturally and they are markedly different from naturally occurring products. A "bispecific" antibody construct or immunoglobulin is hence an artificial hybrid antibody or immunoglobulin having at least two distinct binding sites with different specificities. Bispecific antibody constructs can be produced by a variety of methods including fusion of hybridomas or linking of Fab' fragments. See, e.g., Songsivilai & Lachmann, Clin. Exp. Immunol. 79:315-321 (1990).

The at least two binding domains and the variable domains of the antibody construct of the present invention may or may not comprise peptide linkers (spacer peptides). The term "peptide linker" comprises in accordance with the present invention an amino acid sequence by which the amino acid sequences of one (variable and/or binding) domain and another (variable and/or binding) domain of the antibody construct of the invention are linked with each other. An essential technical feature of such peptide linker is that it does not comprise any polymerization activity. Among the suitable peptide linkers are those described in U.S. Pat. Nos. 4,751,180 and 4,935,233 or WO 88/09344. The peptide linkers can also be used to attach other domains or modules or regions (such as half-life extending domains) to the antibody construct of the invention.

In the event that a linker is used, this linker is preferably of a length and sequence sufficient to ensure that each of the first and second domains can, independently from one another, retain their differential binding specificities. For peptide linkers which connect the at least two binding domains (or two variable domains) in the antibody construct of the invention, those peptide linkers are preferred which comprise only a few number of amino acid residues, e.g. 12 amino acid residues or less. Thus, peptide linkers of 12, 11, 10, 9, 8, 7, 6 or 5 amino acid residues are preferred. An envisaged peptide linker with less than 5 amino acids comprises 4, 3, 2 or one amino acid(s), wherein Gly-rich linkers are preferred. A particularly preferred "single" amino acid in the context of said "peptide linker" is Gly. Accordingly, said peptide linker may consist of the single amino acid Gly. Another preferred embodiment of a peptide linker is characterized by the amino acid sequence Gly-Gly-Gly-Gly-Ser, i.e. Gly4Ser (SEQ ID NO: 1), or polymers thereof, i.e. (Gly4Ser)x, where x is an integer of 1 or greater (e.g. 2 or 3). The characteristics of said peptide linker, which comprise the absence of the promotion of secondary structures, are known in the art and are described e.g. in Dall'Acqua et al. (Biochem. (1998) 37, 9266-9273), Cheadle et al. (Mol. Immunol. (1992) 29, 21-30) and Raag and Whitlow (FASEB (1995) 9 (1), 73-80). Peptide linkers which furthermore do not promote any secondary structures are preferred. The linkage of said domains to each other can be provided, e.g., by genetic engineering, as described in the examples. Methods for preparing fused and operatively linked bispecific single chain constructs and expressing them in mammalian cells or bacteria are well-known in the art (e.g. WO 99/54440 or Sambrook et al., Molecular Cloning: A Laboratory Manual, Cold Spring Harbor Laboratory Press, Cold Spring Harbor, New York, 2001).

According to a particularly preferred embodiment, and as documented in the appended examples, the AMG 701 and AMG 330 antibody constructs of the invention are each a "bispecific single chain antibody construct", more preferably a bispecific "single chain Fv" (scFv). Although the two domains of the Fv fragment, VL and VH, are coded for by separate genes, they can be joined, using recombinant methods, by a synthetic linker—as described hereinbefore—that enables them to be made as a single protein chain in which the VL and VH regions pair to form a monovalent molecule; see e.g., Huston et al. (1988) Proc. Natl. Acad. Sci USA 85:5879-5883). These antibody fragments are obtained using conventional techniques known to those with skill in the art, and the fragments are evaluated for function in the same manner as are whole or full-length antibodies. A single-chain variable fragment (scFv) is hence a fusion protein of the variable region of the heavy chain (VH) and of the light chain (VL) of immunoglobulins, usually connected with a short linker peptide of about ten to about 25 amino acids, preferably about 15 to 20 amino acids. The linker is usually rich in glycine for flexibility, as well as serine or threonine for solubility, and can either connect the N-terminus of the VH with the C-terminus of the VL, or vice versa. This protein retains the specificity of the original immunoglobulin, despite removal of the constant regions and introduction of the linker.

Bispecific single chain molecules are known in the art and are described in WO 99/54440, Mack, J. Immunol. (1997), 158, 3965-3970, Mack, PNAS, (1995), 92, 7021-7025, Kufer, Cancer Immunol. Immunother., (1997), 45, 193-197, Löffler, Blood, (2000), 95, 6, 2098-2103, Brühl, Immunol., (2001), 166, 2420-2426, Kipriyanov, J. Mol. Biol., (1999), 293, 41-56. Techniques described for the production of single chain antibodies (see, inter alia, U.S. Pat. No. 4,946,778) can be adapted to produce single chain antibody constructs specifically recognizing (an) elected target(s).

Bivalent (also called divalent) or bispecific single-chain variable fragments (bi-scFvs or di-scFvs having the format (scFv) 2 can be engineered by linking two scFv molecules (e.g. with linkers as described hereinbefore). If these two scFv molecules have the same binding specificity, the resulting (scFv) 2 molecule will preferably be called bivalent (i.e. it has two valences for the same target epitope). If the two scFv molecules have different binding specificities, the resulting (scFv) 2 molecule will preferably be called bispecific. The linking can be done by producing a single peptide chain with two VH regions and two VL regions, yielding tandem scFvs (see e.g. Kufer P. et al., (2004) Trends in Biotechnology 22 (5): 238-244). Another possibility is the creation of scFv molecules with linker peptides that are too short for the two variable regions to fold together (e.g. about five amino acids), forcing the scFvs to dimerize. This type is known as diabodies (see e.g. Hollinger, Philipp et al., (July 1993) Proceedings of the National Academy of Sciences of the United States of America 90 (14): 6444-8).

As described herein above, the invention provides a preferred embodiment wherein the antibody construct is in a format selected from the group consisting of (scFv) 2, scFv-single domain mAb, diabodies and oligomers of any of the those formats.

According to an also preferred embodiment of the antibody construct of the invention the heavy chain (VH) and of the light chain (VL) of a binding domain binding either to the target antigen CD3 and CD33 or BCMA are not directly connected via an above described peptide linker but the binding domain is formed due to the formation of a bispecifc molecule as described for the diabody. Thus, the VH chain of the CD3 binding domain may be fused to the VL of the CD33 or BCMA binding domain via such peptide linker, while the VH chain of the CD3 binding domain is fused to the VL of the CD33 or BCMA binding domain via such peptide linker.

The terms "amino-terminal" and "carboxyl-terminal" and their shortened forms "N-terminus" and "C-terminus" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

As used herein, the term "amino acid" refers to either natural and/or unnatural or synthetic amino acids, including glycine and both the D and L optical isomers, amino acid analogs and peptidomimetics, including without limitation N-acetyl analogs of D or L optical isomers (e.g., N-acetyl arginine). In some aspects, the term amino acid refers to monomeric amino acids.

Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, for example, Sambrook et al. (2001), Molecular Cloning: A Laboratory Manual, 3rd ed., Cold Spring Harbor Laboratory Press, Cold Spring Harbor, N.Y. and Ausubel et al. (1992), Current Protocols in Molecular Biology, Greene Publishing Associates, and Harlow and Lane (1990), Antibodies: A Laboratory Manual, Cold Spring Harbor Laboratory Press, Cold Spring Harbor, N.Y. Any enzymatic reactions and purification techniques are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

Use of Intermediate Formulated Concentrations

The goal of protein formulation is to transform a highly purified, recombinant protein solution (drug substance) into a stable, efficacious biopharmaceutical dosage form. Kamerzell et al. (2011), 63 (13): 1118-59 (incorporated by reference). The first step, often called preformulation characterization, involves determining the protein's physicochemical properties and pathways of instability, which allows for design of formulations containing various excipients to ensure protein stability under defined storage conditions. At the same time, analytical methods to monitor the protein's physicochemical integrity and biological activity under formulation conditions (e.g., in the presence of excipients) need to be developed, along with specifications to define acceptable limits to any changes in these parameters. Specific formulations at different protein concentrations with targeted levels of various pharmaceutical excipients are then experimentally tested to ensure stability, solubility and tonicity over the shelf life. In addition, the primary container is selected (e.g., vial, cartridge or prefilled syringe) to store the protein-excipient mixture and facilitate parenteral administration by the patient or a medical professional. The entire biopharmaceutical drug or vaccine dosage form (protein, excipients, primary container, and delivery device) must be designed for both scalability, to allow for commercial manufacturing under sterile conditions, and to meet all regulatory guidelines for the production and testing of biopharmaceutical dosage forms for human use.

Formulation development generally starts with identifying the right pH and buffer system through a biophysical screening strategy. Buffers are added to the protein solution to stabilize pH, which in turn stabilizes the protein because a protein's stability is generally linked to a characteristic, narrow pH range. See Garidel and Bassarab (2009), "Impact of formulation design on stability and quality," in: Quality for Biologics: Critical Quality Attributes, Process and Change Control, Production Variation, Characterisation, Impurities and Concerns, Biopharm Knowledge Publishing, London, UK, pp. 94-113 (incorporated by reference). Other formulation excipients, such as stabilizers (e.g., sugars), bulking agents (e.g., mannitol), and surfactants (e.g., polysorbate 20) are then added to the buffered protein solution. For a lyophilized formulation, such a formulation mixture in liquid form is then lyophilized.

In lyophilization as in other drug product processes, a key control is therapeutic protein fill weight to deliver the required dose to the patient. For higher concentration products, a simple strategy of controlling the product concentration at the formulation stage, followed by fill weight control as part of the fill process, is adequate. For very low dose delivery in micro or even milligrams of product, however, this simple strategy for ensuring dose delivery begins to have problems in ensuring that the patient can receive the required dose. Related concerns are that the product label may not reflect the product within the container and that one may have difficulty extracting the material for dosing. A need exists, therefore, for a process providing greater control over the fill weight of a therapeutic protein in a lyophilized pharmaceutical formulation.

As noted above, a simple strategy of controlling the product concentration at the formulation stage, followed then by fill weight control as part of the fill process is adequate for higher concentrations of therapeutic protein but can lead to problems in lower concentrations. The design space for fill weight control for low dose product when the fill weight and formulation target are controlled separately shows a higher variability, with a greater likelihood the product will not meet the release specification. Due to manufacturing variability, precisely controlling the formulated bulk is not achievable due to the scale of the process and the inherent variability of the equipment in manufacturing. Another issue is that increased variability is inherent in the lyophilized product because the product must be reconstituted, which is also a variable process.

A typical control strategy (shown in FIG. 1) would have a greater than 50% probability of having a failed protein concentration result. In FIG. 1, the observed overall variability of lyophilized homogeneity data is 0.01 mg/mL. To assure minimal capability, the average operating range must be constrained such that it corresponds to a specification range "stepped-in" by 3*0.01=0.03 mg/mL. A process that is targeted within the white space has quality of less than 0.1% of Out of Specification (OOS) vials per batch. A process that is targeted within the shaded area, in contrast, has greater OOS rates. As can be seen from FIG. 1, the current operating range (large square) contains edges of failure of the desired formulation. An effective operating range (smaller rectangle in FIG. 1), however, requires tighter fill tolerances than can be achieved as part of both the formulation variability and the filler weight control.

Figure 2:
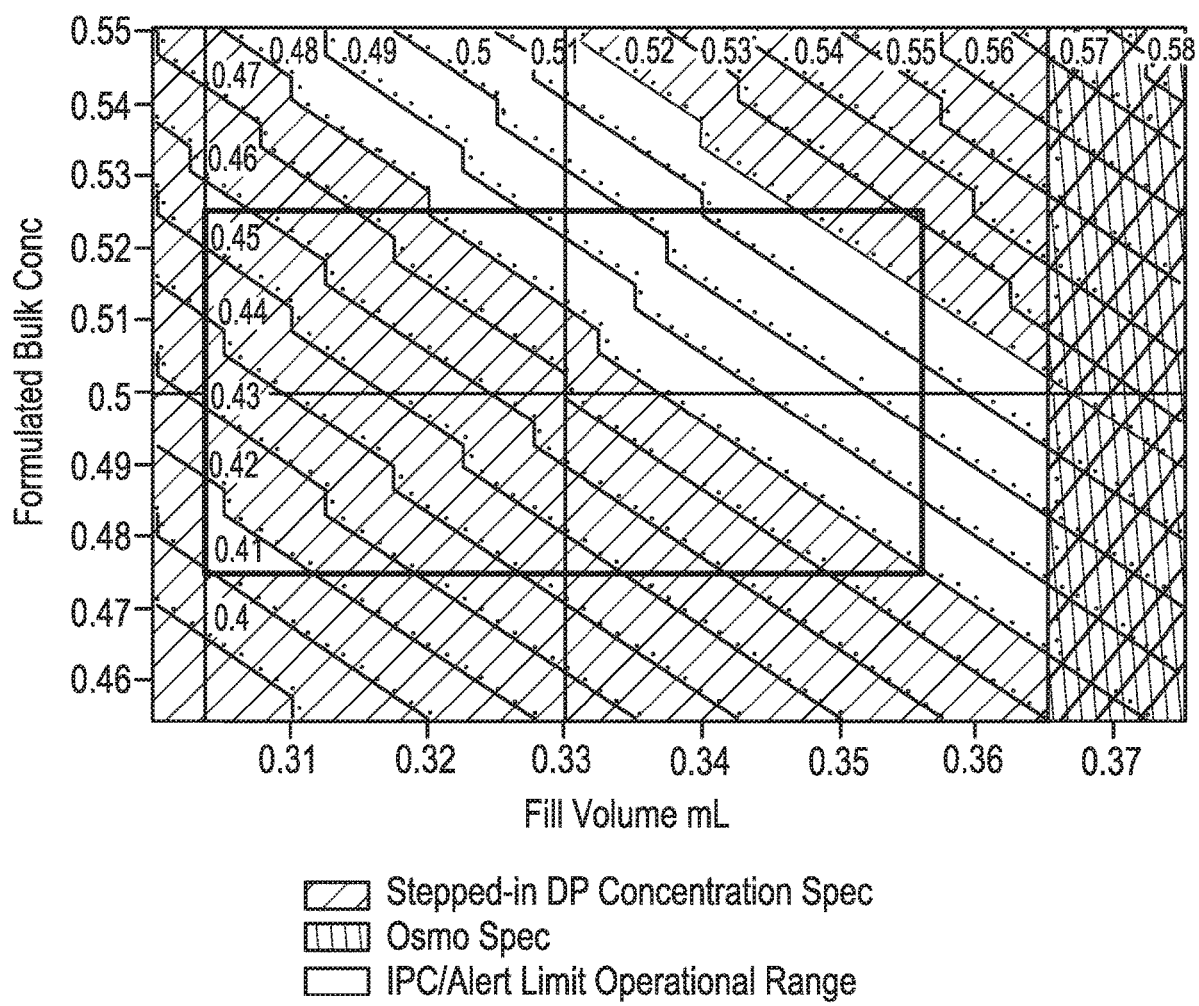
FIG. 2 is a response surface map showing an example design space for a low dose product in which osmolality is considered in addition to bulk concentration and fill volume. The light gray region shows the stepped-in drug product concentration specification wherein method/reconstitution variability would have a greater than 50% probability of having a failed protein concentration result. The dark gray area shows the osmolality specification. The rectangle shows the design space range for the fill weight (x-axis) and the formulated bulk concentration (y-axis) in-process control (IPC)/alert limit operational range (ALOR).

Thus, a process that also needs to consider other product quality attributes (e.g., osmolality, pH) as well as protein concentration might not be producible or viable by the standard methodology. FIG. 2 shows an example design space in which an osmolality specification is considered. The gray coloring shows the extensive failure conditions within the IPC/alert limit operation range.

Figure 3:
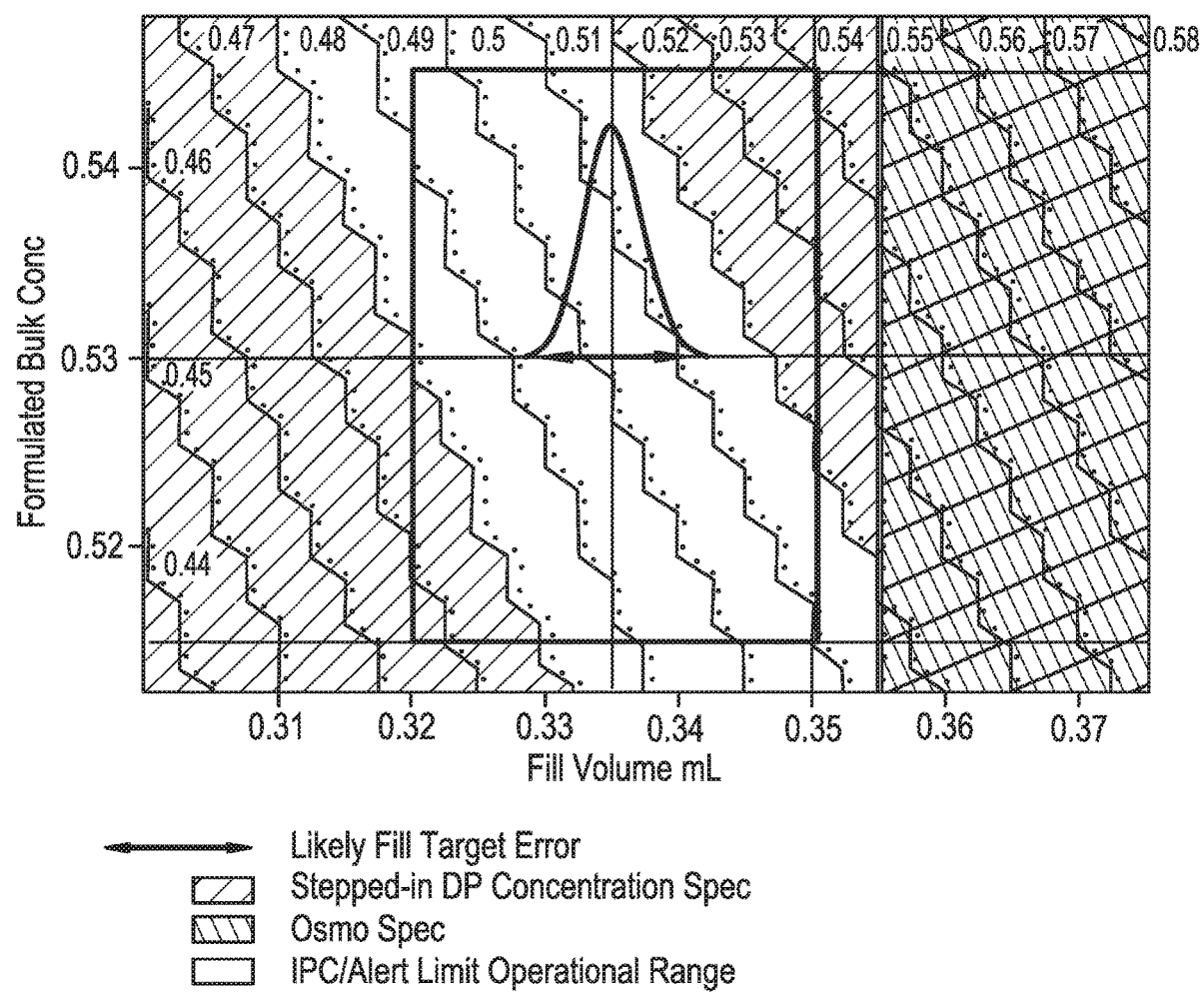
FIG. 3 is a response surface map showing an example of a viable but not fault-tolerant fill weight and formulation control strategy. The curve and two-headed arrow show the likely fill target error. The light gray area represents the stepped-in drug product concentration specification, with the light gray area showing where method/reconstitution variability would have a greater than 50% probability of having a failed protein concentration result. The dark gray area defines the osmolality specification. The rectangle shows the IPC/ALOR.

Standard methodology can also result in a viable but not fault-tolerant fill weight and formulation control strategy (see FIG. 3). As in FIG. 1, the IPC/ALOR contains areas that do not meet the drug product concentration specification. Within the area that does meet the drug product concentration specification (white area within the IPC/ALOR), there is very little room for error in the fill target. Thus, as shown in FIG. 3, standard methodology may result in a process with difficulty at the edge of range control, viable but without sufficient fault tolerance . . .

Figure 4:
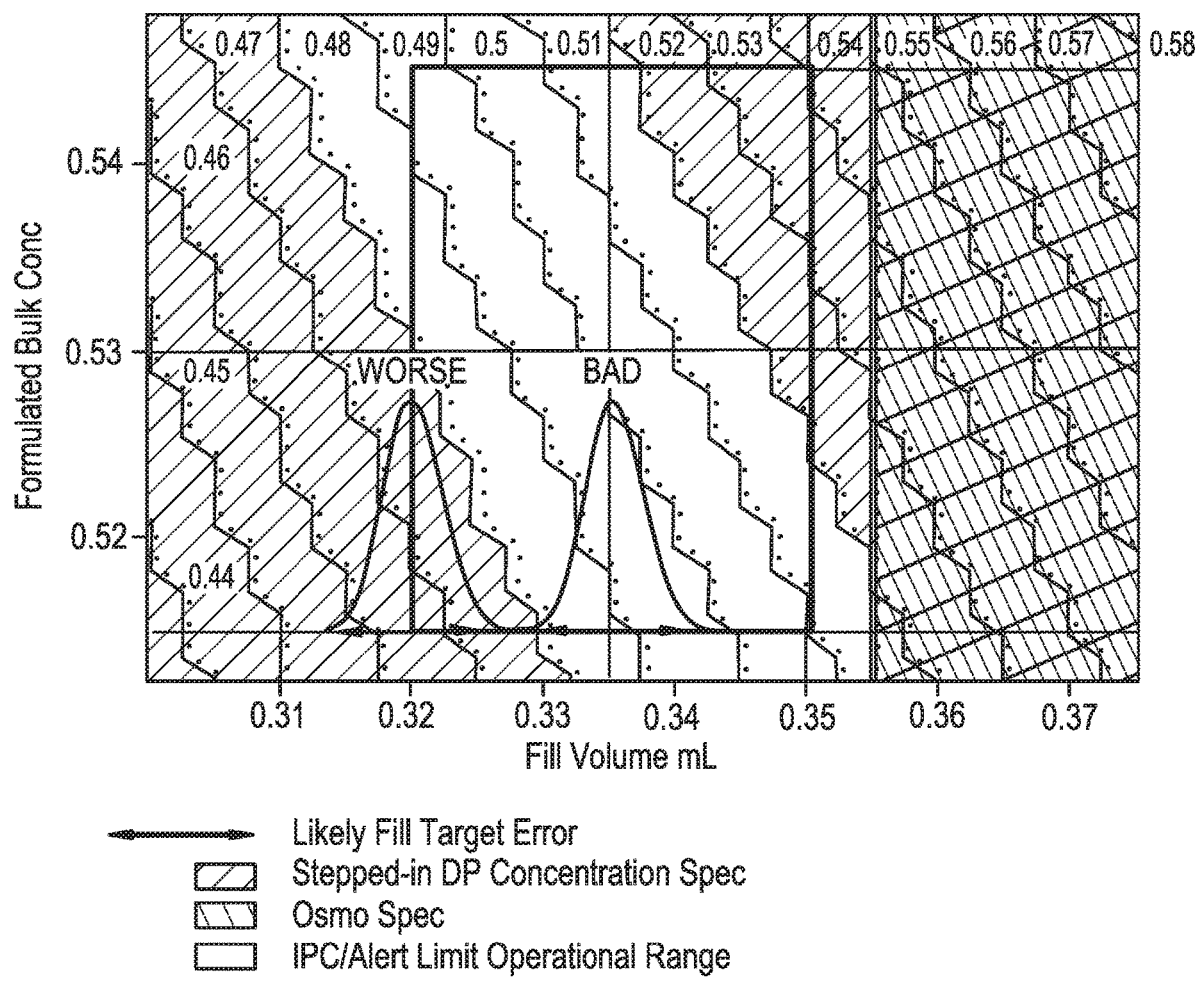
FIG. 4 is a response surface map showing an example of a fill weight and formulation control strategy with difficulty at the edge of range control, with an expected lower formulated bulk and lower fill weight. The left curve and two-headed arrow shows the likely fill target error at a low fill volume. The right curve and two-headed arrow show the likely fill target error at a higher fill volume. The light gray area represents the stepped-in drug product concentration specification, with the light gray area showing where method/reconstitution variability would have a greater than 50% probability of having a failed protein concentration result. The dark gray area defines the osmolality specification. The rectangle shows the IPC/ALOR.

An increase in fill volume might not be enough of a process variation to create a viable formulation with adequate fault tolerance. FIG. 4 is a response surface map in which fill volume is increased. The fill target range may be brought within the IPC/ALOR and product specifications but fault tolerance may remain inadequate. The fill weight range over the allowable range of the formulated bulk concentration has insufficient fault tolerance.

Figure 5:
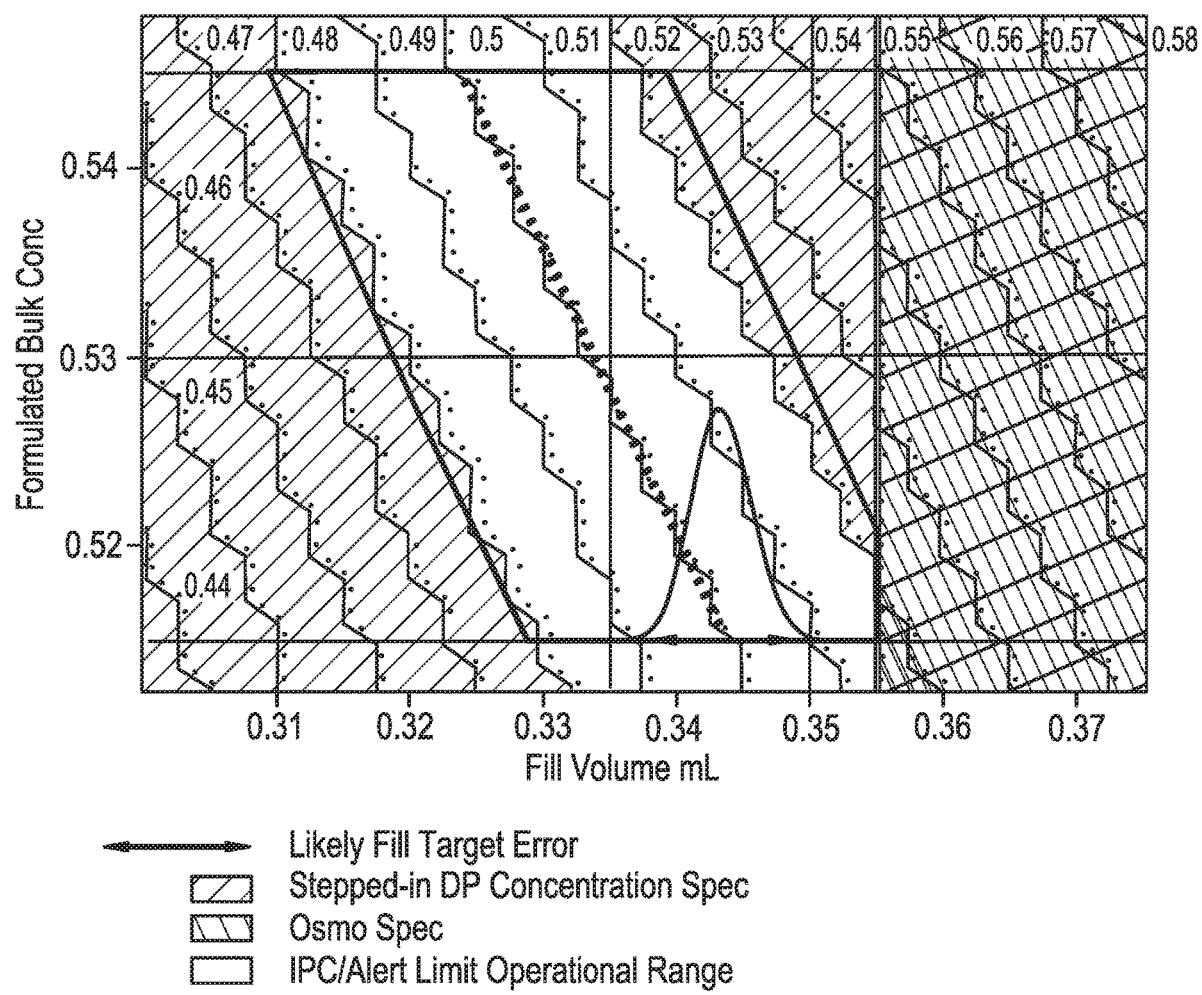
FIG. 5 is a response surface map showing an example of a combined strategy of using the formulating bulk result to then adjust the fill weight set point based upon a total product dose in the vial target, resulting in a viable, fault-tolerant lyophilized drug process. The curve and two-headed arrow show the likely fill target error. The light gray area defines the stepped-in drug product concentration specification as in FIGS. 1 to 4. The dark gray area defines the osmolality specification. The rhomboid shows the IPC/ALOR, cut off by the osmolality specification at the highest fill volumes within the IPC/ALOR.

If the formulated bulk result is used to then adjust the therapeutic protein fill weight, the operating range may be changed enough to enable a formulation that is both viable and sufficiently fault-tolerant. As shown in FIG. 5, the modified operating range (IPC/ALOR) allows for the expected fill target range to be well within the concentration and osmolality specifications. In this way, the fill target range can be provided within the concentration and other specifications with sufficient fault tolerance.

To date, this technique has been used for a low dose stock keeping unit (SKU) for romiplostim (Nplate®) low dose SKU, blinatumomab (Blincyto®), infliximab, and trastuzumab. Details on use of this technique appear in the Working Examples hereinafter.

Excipients in General

One challenge in formulations is stabilizing the product against the stresses of manufacturing, shipping and storage, which can be accomplished by certain formulation excipients. In general, excipients can be classified on the basis of the mechanisms by which they stabilize proteins against various chemical and physical stresses. Some excipients alleviate the effects of a specific stress or regulate a particular susceptibility of a specific protein. Other excipients more generally affect the physical and covalent stabilities of proteins.

Common excipients of liquid and lyophilized protein formulations appear in Table 2 (see Kamerzell et al. (2011), Advanced Drug Delivery Rev. 63 (13): 1118-59).

TABLE 2

Excipient components of protein formulations

| Excipient component | Function | Examples |
|---|---|---|
| Buffers | Maintaining pH of solution<br>Buffer-ion specific interactions with protein | Citrate<br>Succinate<br>Acetate<br>Glutamate<br>Aspartate<br>Histidine<br>Phosphate<br>Tris<br>Glycine |
| Sugars and carbohydrates | Stabilizing protein<br>Tonicifying agents<br>Carrier for inhaled drugs (lactose)<br>Dextrose solutions during IV administration | Sucrose<br>Trehalose<br>Sorbitol<br>Mannitol<br>Glucose<br>Lactose<br>Cyclodextrin derivatives |
| Stabilizers and bulking agents | Enhancing product elegance and preventing blowout<br>Providing structural strength to a lyo cake | Mannitol<br>Glycine |
| Osmolytes | Stabilizing against environmental stress (temperature, dehydration) | Sucrose<br>Trehalose<br>Sorbitol<br>Glycine<br>Proline<br>Glutamate<br>Glycerol<br>Urea |
| Amino acids | Specific interactions with protein<br>Antioxidant (His, Met)<br>Buffering, tonicifying | Histidine<br>Arginine<br>Glycine<br>Proline<br>Lysine<br>Methionine<br>Aa mixtures (e.g., glu/arg) |

TABLE 2-continued

Excipient components of protein formulations

| Excipient component | Function | Examples |
|---|---|---|
| Proteins and polymers | Competitive inhibitors of protein adsorption<br>Bulking agents for lyophilization<br>Drug delivery vehicles | HSA<br>PVA<br>PVP<br>PLGA<br>PEG<br>Gelatin<br>Dextran<br>Hydroxyethyl starch<br>HEC<br>CMC |
| Anti-oxidants | Preventing oxidative protein damage<br>Metal ion binders (if a metal is included as a co-factor or is required for protease activity)<br>Free radical scavengers | Reducing agents<br>Oxygen scavengers<br>Free radical scavengers<br>Chelating agents (e.g., EDTA, EGTA, DTPA)<br>Ethanol |
| Metal ions | Protein co-factors<br>Coordination complexes (suspensions) | Magnesium<br>Zinc |
| Specific ligands | Stabilizers of native conformation against stress-induced unfolding<br>Providing conformation flexibility | Metals<br>Ligands<br>Amino acids<br>Polyanions |
| Surfactants | Competitive inhibitor of protein adsorption<br>Competitive inhibitor of protein surface denaturation<br>Liposomes as drug delivery vehicles<br>Inhibitor of aggregation during lyophilization<br>Reducer of reconstitution times of lyophilized products | Polysorbate 20<br>Polysorbate 80<br>Poloxamer188<br>Anionic surfactants (e.g., sulfonates and sulfosuccinates)<br>Cationic surfactants<br>Zwitterionic surfactants |
| Salts | tonicifying agents<br>stabilizing or destabilizing agents for proteins, especially anions | NaCl<br>KCl<br>NaSO$_4$ |
| Preservatives | Protection against microbial growth in formulation | Benzyl alcohol<br>M-cresol<br>Phenol |

Other excipients are known in the art and can be found in Powell et al. (1998), "Compendium of Excipients for Parenteral Formulations," PDA J. Pharm. Sci. Tech., 52:238-311, which is hereby incorporated by reference.

Given the teachings and guidance provided herein, those skilled in the art will know what amount or range of excipient can be included in any particular formulation to achieve a biopharmaceutical formulation of the invention. For example, the amount and type of a salt to be included in a biopharmaceutical formulation of the invention can be selected based on the desired osmolality (i.e., isotonic, hypotonic or hypertonic) of the final solution as well as the amounts and osmolality of other components to be included in the formulation. Similarly, by exemplification with reference to the type of polyol or sugar included in a formulation, the amount of such an excipient will depend on its osmolality.

Those skilled in the art can determine what amount or range of excipient can be included in any particular formulation to achieve a biopharmaceutical formulation of the invention that promotes retention in stability of the biopharmaceutical. For example, the amount and type of a salt to be included in a biopharmaceutical formulation of the invention can be selected based on to the desired osmolality (i.e., isotonic, hypotonic or hypertonic) of the final solution as well as the amounts and osmolality of other components to be included in the formulation. Similarly, by exemplification with reference to the type of polyol or sugar included in a formulation, the amount of such an excipient will depend on its osmolality.

About 5% (weight/volume) sorbitol, for example, can achieve isotonicity while about 9% (weight/volume) of a sucrose excipient is needed to achieve isotonicity. Selection of the amount or range of concentrations of one or more excipients that can be included within a biopharmaceutical formulation of the invention has been exemplified above by reference to salts, polyols and sugars. However, those skilled in the art will understand that the considerations described herein and further exemplified by reference to specific excipients are equally applicable to all types and combinations of excipients including, for example, salts, amino acids, other tonicity agents, surfactants, stabilizers, bulking agents, cryoprotectants, lyoprotectants, anti-oxidants, metal ions, chelating agents and/or preservatives.

Further, where a particular excipient is reported in a formulation by, e.g., percent (%) w/v, those skilled in the art will recognize that the equivalent molar concentration of that excipient is also contemplated.

Those having ordinary skill in the art would recognize that the concentrations of the aforementioned excipients share an interdependency within a particular formulation. By way of example, the concentration of a bulking agent may be lowered where, for example, there is a high protein/peptide concentration or a high stabilizing agent concentration. In addition, a person having ordinary skill in the art would recognize that, in order to maintain the isotonicity of a particular formulation in which there is no bulking agent, the concentration of a stabilizing agent would be adjusted accordingly (i.e., a "tonicifying" amount of stabilizer would be used).

Buffers

Solution pH affects the chemical integrity of a protein's amino acid residues (e.g., Asn deamidation and Met oxidation) and maintenance of its higher order structure. Those skilled in the art thus use buffering agents to control solution pH and optimize protein stability. Maximal stability of a protein drug is usually within a narrow pH range. Several approaches (e.g., accelerated stability studies and calorimetric screening studies) are useful for this purpose (Remmele et al. (1999), Biochemistry, 38 (16): 5241-7). Once a formulation is finalized, the drug product must be manufactured and maintained within a predefined specification throughout its shelf-life. Hence, buffering agents are almost always employed to control pH in the formulation.

Organic acids, phosphates and Tris have been employed routinely as buffers in protein formulations (see Table 3). The buffer capacity of the buffering species is maximal at a pH equal to the pKa and decreases as pH increases or decreases away from this value. Ninety percent of the buffering capacity exists within one pH unit of its pKa. Buffer capacity also increases proportionally with increasing buffer concentration.

TABLE 3

Commonly used buffering agents and their $pK_a$ values

| Buffer | $pK_a$ | Example drug product |
|---|---|---|
| Acetate | 4.8 | Neupogen ®, Neulasta ® |
| Succinate | $pK_{a1} = 4.8$, $pK_{a2} = 5.5$ | Actimmune ® |
| Citrate | $pK_{a1} = 3.1$, $pK_{a2} = 4.8$, $pK_{a3} = 6.4$ | Humira ® |
| Histidine (imidazole) | 6.0 | Xolair ® |
| phosphate | $pK_{a1} = 2.15$, $pK_{a2} = 7.2$, $pK_{a3} = 12.3$ | Enbrel ® (liquid formulation) |
| Tris | 8.1 | Leukine ® |

In addition to the foregoing, some therapeutic proteins may be self-buffering at a pharmaceutically relevant concentration. Formulations of such proteins might not need to include a conventional buffer at all. See US patent application 2012/0028877, which is hereby incorporated by reference.

Sugars and Carbohydrates

Sugars are frequently used to stabilize proteins in both liquid and lyophilized formulations. Disaccharides such as sucrose and trehalose are thought to stabilize proteins by preferential hydration at high concentrations in the liquid state and by specific interactions with proteins and formation of viscous glassy matrices in the solid state. Sugar molecules can increase the viscosity of monoclonal antibody solutions, presumably due to a preferential hydration mechanism. Sugar alcohols such as sorbitol can stabilize proteins in solution and in the lyophilized state. Mannitol is often used as a bulking agent in lyophilized formulations. Lactose is used as a carrier molecule for inhaled formulations of proteins. Cyclodextrin derivatives can stabilize proteins in liquid formulations of antibodies, vaccine antigens, and such smaller proteins as growth factors, interleukin-2 and insulin.

Stabilizers and bulking agents

Bulking agents are typically used in lyophilized formulations to enhance product elegance and to prevent blowout. Conditions in the formulation are generally designed so that the bulking agent crystallizes out of the frozen amorphous phase (either during freezing or annealing above the Tg') giving the cake structure and bulk. Mannitol and glycine are examples of commonly used bulking agents.

Stabilizers include a class of compounds that can serve as cryoprotectants, lyoprotectants, and glass forming agents. Cryoprotectants act to stabilize proteins during freezing or in the frozen state at low temperatures (P. Cameron, ed., Good Pharmaceutical Freeze-Drying Practice, Interpharm Press, Inc., Buffalo Grove, IL, (1997)). Lyoprotectants stabilize proteins in the freeze-dried solid dosage form by preserving the native-like conformational properties of the protein during dehydration stages of freeze-drying. Glassy state properties have been classified as "strong" or "fragile" depending on their relaxation properties as a function of temperature. It is important that cryoprotectants, lyoprotectants, and glass forming agents remain in the same phase with the protein in order to impart stability. Sugars, polymers, and polyols fall into this category and can sometimes serve all three roles.

Polyols encompass a class of excipients that includes sugars, (e.g. mannitol, sucrose, sorbitol), and other polyhydric alcohols (e.g., glycerol and propylene glycol). The polymer polyethylene glycol (PEG) is included in this category. Polyols are commonly used as stabilizing excipients and/or isotonicity agents in both liquid and lyophilized parenteral protein formulations. With respect to the Hofmeister series, the polyols are kosmotropic and are preferentially excluded from the protein surface. Polyols can protect proteins from both physical and chemical degradation pathways. Preferentially excluded co-solvents increase the effective surface tension of solvent at the protein interface whereby the most energetically favorable protein conformations are those with the smallest surface areas.

Mannitol is a popular bulking agent in lyophilized formulations because it crystallizes out of the amorphous protein phase during freeze-drying lending structural stability to the cake (e.g. Leukine®, Enbrel®-Lyo, Betaseron®). It is generally used in combination with a cryo and/or lyoprotectant like sucrose. Because of the propensity of mannitol to crystallize under frozen conditions, sorbitol and sucrose are the preferred tonicity agents/stabilizers in liquid formulations to protect the product against freeze-thaw stresses encountered during transport or when freezing bulk prior to manufacturing. Sorbitol and sucrose are far more resistant to crystallization and therefore less likely to phase separate from the protein. It is interesting to note that while mannitol has been used in tonicifying amounts in several marketed liquid formulations such as Actimmune®, Forteo®, and Rebif®, the product labels of these drugs carry a 'Do Not Freeze' warning. The use of reducing sugars (containing free aldehyde or ketone groups) such as glucose and lactose should be avoided because they can react and glycate surface lysine and arginine residues of proteins via the Maillard reaction of aldehydes and primary amines (Chevalier F, et al., *Nahrung*, 46 (2): 58-63 (2002); Humeny A, et al., *J Agric Food Chem*. 50 (7): 2153-60 (2002)). Sucrose can hydrolyze to fructose and glucose under acidic conditions (Kautz C. F. and Robinson A. L., *JACS*, 50 (4) 1022-30 (1928)), and consequently may cause glycation.

In particular embodiments of the present compositions, a stabilizer (or a combination of stabilizers) is added to a lyophilization formulation to prevent or reduce lyophilization-induced or storage-induced aggregation and chemical degradation. A hazy or turbid solution upon reconstitution indicates that the protein has precipitated. The term "stabilizer" means an excipient capable of preventing aggregation or other physical degradation, as well as chemical degradation (for example, autolysis, deamidation, oxidation, etc.) in an aqueous and solid state. Stabilizers that are conventionally employed in pharmaceutical compositions include, but are not limited to, sucrose, trehalose, mannose, maltose, lactose, glucose, raffinose, cellobiose, gentiobiose, isomaltose, arabinose, glucosamine, fructose, mannitol, sorbitol, glycine, arginine HCL, poly-hydroxy compounds, including polysaccharides such as dextran, starch, hydroxyethyl starch, cyclodextrins, N-methyl pyrollidene, cellulose and hyaluronic acid, sodium chloride, Carpenter et al. (1991), Develop. Biol. Standard 74:225.

Osmolytes

Osmolytes currently used as protein formulation excipients are listed in Table 2. Other osmolytes commonly found in nature that may be useful as excipients include taurine, betaine, trimethylamine N-oxide (TMAO), choline-O-sulfate, and sarcosine.

Proteins and Polymers

Protein-based excipients add complexity to the formulation, especially in developing analytical methods to monitor the stability of the protein-based drug or vaccine in the presence of a protein-based excipient. Polymers have been evaluated as excipients (e.g., as bulking agents) in lyophilized protein formulations. Controlled release formulations of protein drugs and vaccines are being studied in which proteins are formulated with polymers such as poly (lactic-co-glycolic acid) (PLGA) and polyethylene glycol (PEG). Many additional water-soluble polymers (e.g., hydroxyethyl cellulose (HEC), carboxymethyl cellulose (CMC)) have been utilized for topical formulations of protein drugs.

PEG can stabilize proteins by two different temperature-dependent mechanisms. At lower temperatures, it is preferentially excluded from the protein surface but has been shown to interact with the unfolded form of the protein at higher temperature given its amphipathic nature (Lee and Lee (1987), Biochemistry, 26 (24): 7813-9). It may protect proteins via preferential exclusion at lower temperatures but possibly by reducing the number of productive collisions between unfolded molecules at higher temperatures. PEG is also a cryoprotectant and has been employed in Recombinate®, a lyophilized formulation of recombinant Antihemophilic Factor.

Anti-Oxidants

Many different sources may oxidize protein residues. Oxidative protein damage can be minimized by carefully controlling the manufacturing process and storage of the product, including such factors as atmospheric oxygen, temperature, light exposure, and chemical contamination. Where such controls are inadequate, anti-oxidant excipients can be included in the formulation.

The most commonly used pharmaceutical antioxidant excipients are reducing agents, oxygen/free-radical scavengers, or chelating agents. Antioxidants in therapeutic protein formulations must be water-soluble and remain active throughout the product shelf-life. Reducing agents and oxygen/free-radical scavengers work by ablating active oxygen species in solution. Chelating agents (e.g., EDTA) can be effective by binding trace metal contaminants that promote free-radical formation. In the liquid formulation of acidic fibroblast growth factor, for example, EDTA inhibits metal ion-catalyzed oxidation of cysteine residues. EDTA has been used in marketed products like Kineret® and Ontak®.

Metal Ions

In general, transition metal ions are undesired in protein formulations because they can catalyze physical and chemical degradation reactions in proteins. Specific metal ions are included in formulations, however, when they act as co-factors to proteins. Metal ions may also be used in suspension formulations of proteins where they form coordination complexes (e.g., zinc suspension of insulin). The use of magnesium ions (10-120 mM) has been proposed to inhibit the isomerization of aspartic acid to isoaspartic acid (WO 2004/039337).

Metal ions were found to confer stability and/or increased activity in a formulation of human deoxyribonuclease (rhDNase, Pulmozyme®). $Ca^{+2}$ ions (up to 100 mM) increased the stability of the enzyme through a specific binding site (Chen et al. (1999), J Pharm Sci. 88 (4): 477-82). In fact, removal of calcium ions from the solution with EGTA caused an increase in deamidation and aggregation. However, this effect was observed only with $Ca^{+2}$ ions; other divalent cations—$Mg^{+2}$, $Mn^{+2}$ and $Zn^{+2}$-were observed to destabilize rhDNase.

Similar effects were observed in formulation of Factor VIII. $Ca^{+2}$ and $Sr^{+2}$ ions stabilized the protein while others like $Mg^{+2}$, $Mn^{+2}$ and $Zn^{+2}$, $Cu^{+2}$ and $Fe^{+2}$ destabilized it (Fatouros, et al. (1997), Int. J. Pharm., 155, 121-131). In a separate study with Factor VIII, a significant increase in aggregation rate was observed in the presence of $Al^{+3}$ ions (Derrick et al. (2004), J. Pharm. Sci., 93 (10): 2549-57). The authors note that other excipients like buffer salts are often contaminated with $Al^{+3}$ ions and illustrate the need to use excipients of appropriate quality in formulated products. Vaccines containing live or killed attenuated picornaviruses, such as Hepatitis A and polio, are conformationally stabilized by magnesium. Metal ions such as calcium, magnesium and zinc improve the stability of oxytocin in an aqueous solution Insulin can bind zinc, leading to the formation of dimers and hexamers in a crystalline form, which allows for the preparation of different formulations with different in vivo release profiles. The chemical and thermal stability of the hexamer insulin formulation varies in the presence of different levels of zinc and phenol.

Specific Ligands

One approach to improve the conformational stability of protein therapeutic drugs is to take advantage of the protein's inherent ligand binding sites. For example, Pulmozyme® not only requires bivalent metal ions for its enzymatic activity, it has improved conformational stability in the presence of calcium ions. Both acidic and basic fibroblast growth factors (aFGF and bFGF) have been evaluated clinically for their ability to promote wound healing, and both proteins naturally bind to the highly negatively charged proteoglycans on cell surfaces. A variety of other highly negatively charged compounds also bind and dramatically stabilize aFGF by interaction with the protein's polyanion binding site.

Surfactants

Protein molecules have a high propensity to interact with surfaces, making them susceptible to adsorption and denaturation at air-liquid, vial-liquid, and liquid-liquid (silicone oil) interfaces. This degradation pathway is inversely dependent on protein concentration and results in soluble or insoluble protein aggregates or the loss of protein from solution through adsorption to surfaces. In addition to container surface adsorption, surface-induced degradation is exacerbated with physical agitation, as would be experienced during shipping and handling.

Surfactants are commonly used in protein formulations to prevent surface-induced degradation. Surfactants are amphipathic molecules with the capability of out-competing proteins for interfacial positions. Hydrophobic portions of the surfactant molecules occupy interfacial positions (e.g., air/liquid), while hydrophilic portions of the molecules remain oriented towards the bulk solvent. At sufficient concentrations (typically around the detergent's critical micellar concentration), a surface layer of surfactant molecules serve to prevent protein molecules from adsorbing at the interface. Thereby, surface-induced degradation is minimized.

The most commonly used surfactants are the non-ionic fatty acid esters of sorbitan polyethoxylates—i.e., polysorbate 20 and polysorbate 80 (e.g., in the drug products Avonex®, Neupogen®, Neulasta®). The two differ only in the length of the aliphatic chain that imparts hydrophobic character to the molecules, C-12 and C-18, respectively. Polysorbate 80 is more surface-active and has a lower critical micellar concentration than polysorbate 20. Both polysorbate 20 and polysorbate 80 have been shown to protect against agitation-induced aggregation. Polysorbate 20 and 80 also protect against stress induced by freezing, lyophilization and reconstitution. Both polysorbate 20 and 80 may contain peroxides which can oxidize proteins and they themselves may degrade by either oxidation or hydrolysis with varying effects on protein stability. It can also be difficult to control the level of polysorbate 20 or 80 in formulations due to their complex behavior during membrane filtration (especially at concentrations in which polysorbates form micelles in solution). The surfactant poloxamer 188 has also been used in several marketed liquid products, such Gonal-F®, Norditropin®, and Ovidrel®. It is generally believed that non-ionic surfactants stabilize proteins primarily by outcompeting protein molecules for hydrophobic surfaces (e.g., air-water interfaces), thereby preventing proteins from unfolding at these hydrophobic interfaces. Non-ionic surfactants can also block protein molecules from adsorbing to other hydrophobic surfaces present during processing. In addition, non-ionic surfactants may directly interact with hydrophobic regions in protein molecules. Monoclonal antibodies can affect the critical micelle concentration of polysorbate 20 compared to buffer alone.

Detergents can also affect the thermodynamic conformational stability of proteins. Here again, the effects of a given excipient will be protein-specific. For example, polysorbates have been shown to reduce the stability of some proteins and increase the stability of others. Detergent destabilization of proteins can be rationalized in terms of the hydrophobic tails of the detergent molecules that can engage in specific binding with partially or wholly unfolded protein states. These types of interactions could cause a shift in the conformational equilibrium towards the more expanded protein states (i.e., increasing the exposure of hydrophobic portions of the protein molecule in complement to binding polysorbate). Alternatively, if the protein native state exhibits some hydrophobic surfaces, detergent binding to the native state may stabilize that conformation.

Another aspect of polysorbates is that they are inherently susceptible to oxidative degradation. Often, as raw materials, they contain sufficient quantities of peroxides to cause oxidation of protein residue side-chains, especially methionine. The potential for oxidative damage arising from the addition of stabilizer emphasizes the point that the lowest effective concentrations of excipients should be used in formulations. For surfactants, the effective concentration for a given protein will depend on the mechanism of stabilization. It has been postulated that if the mechanism of surfactant stabilization is related to preventing surface denaturation, then the effective concentration will be around the detergent's critical micellar concentration. Conversely, if the mechanism of stabilization is associated with specific protein-detergent interactions, the effective surfactant concentration will be related to the protein concentration and the stoichiometry of the interaction (Randolph et al. (2002), Pharm Biotechnol., 13:159-75).

Surfactants may also be added in appropriate amounts to prevent surface-related aggregation during freezing and drying (Chang (1996), J. Pharm. Sci. 85:1325). Exemplary surfactants include anionic, cationic, nonionic, zwitterionic, and amphoteric surfactants, including surfactants derived from naturally occurring amino acids. Anionic surfactants include, but are not limited to, sodium lauryl sulfate, dioctyl sodium sulfosuccinate and dioctyl sodium sulfonate, chenodeoxycholic acid, N-lauroylsarcosine sodium salt, lithium dodecyl sulfate, 1-octanesulfonic acid sodium salt, sodium cholate hydrate, sodium deoxycholate, and glycodeoxycholic acid sodium salt. Cationic surfactants include, but are not limited to, benzalkonium chloride or benzethonium chloride, cetylpyridinium chloride monohydrate, and hexadecyltrimethylammonium bromide. Zwitterionic surfactants include, but are not limited to, CHAPS, CHAPSO, SB3-10, and SB3-12. Non-ionic surfactants include, but are not limited to, digitonin, Triton X-100, Triton X-114, TWEEN-20, and TWEEN-80. In another embodiment, surfactants include lauromacrogol 400, polyoxyl 40 stearate, polyoxyethylene hydrogenated castor oil 10, 40, 50 and 60, glycerol monostearate, polysorbate 40, 60, 65 and 80, soy lecithin and other phospholipids such as DOPC, DMPG, DMPC, and DOPG; sucrose fatty acid ester, methyl cellulose and carboxymethyl cellulose.

Salts

Salts are often added to increase the ionic strength of the formulation, which can be important for protein solubility, physical stability, and isotonicity. Salts can affect the physical stability of proteins in a variety of ways. Ions can stabilize the native state of proteins by binding to charged residues on the protein's surface. Alternatively, they can stabilize the denatured state by binding to the peptide groups along the protein backbone (—CONH—). Salts can also stabilize the protein native conformation by shielding repulsive electrostatic interactions between residues within a protein molecule. Electrolytes in protein formulations can also shield attractive electrostatic interactions between protein molecules that can lead to protein aggregation and insolubility.

The effect of salt on the stability and solubility of proteins varies significantly with the characteristics of the ionic species. The Hofmeister series originated in the 1880's as a way to rank order electrolytes based on their ability to precipitate proteins (Cacace et al. (1997), Quarterly Reviews of Biophysics, 30 (3): 241-277). In this report, the Hofmeister series is used to illustrate a scale of protein stabilization effects by ionic and non-ionic co-solutes. In Table C, co-solutes are ordered with respect to their general effects on solution state proteins, from stabilizing (kosmotropic) to destabilizing (chaotropic). In general, the differences in effects across the anions are far greater than that observed for the cations, and, for both types, the effects are most apparent at higher concentrations than are acceptable in parenteral formulations. High concentrations of kosmotropes (e.g., >1 molar ammonium sulfate) are commonly used to precipitate proteins from solution by a process called 'salting-out' where the kosmotrope is preferentially excluded from the protein surface reducing the solubility of the protein in it's native (folded) conformation. Removal or dilution of the salt will return the protein to solution. The term 'salting-in' refers to the use of destabilizing ions (e.g., like guanidine and chloride) that increase the solubility of proteins by solvating the peptide bonds of the protein backbone. Increasing concentrations of the chaotrope will favor the denatured (unfolded) state conformation of the protein as the solubility of the peptide chain increases. The relative effectiveness of ions to 'salt-in' and 'salt-out' defines their position in the Hofmeister series (FIG. 8).

In order to maintain isotonicity in a parenteral formulation, salt concentrations are generally limited to less than 150 mM for monovalent ion combinations. In this concentration range, the mechanism of salt stabilization is probably due to screening of electrostatic repulsive intramolecular forces or attractive intermolecular forces (Debye-Huckel screening). Interestingly, chaotropic salts have been shown to be more effective at stabilizing the protein structure than similar concentrations of kosmotropes by this mechanism. The chaotropic anions are believed to bind more strongly than the kosmotropic ions. With respect to covalent protein degradation, differential effects of ionic strength on this mechanism are expected through Debye-Huckel theory. Accordingly, published reports of protein stabilization by sodium chloride are accompanied by those where sodium chloride accelerated covalent degradation. The mechanisms by which salts affect protein stability are protein specific and may vary significantly as a function of solution pH. An example where an excipient can be useful in enabling the delivery of a protein drug is that of some high concentration antibody formulations. Over the last several years, salts have been shown to be effective in reducing the viscosity of such formulations (Liu et al. (2005, 2006), J. Pharm Sci., 94 (9): 1928-40, erratum in J Pharm Sci., 95 (1): 234-5.

Preservatives

Preservatives are necessary when developing multi-use parenteral formulations that involve more than one extraction from the same container. Their primary function is to inhibit microbial growth and ensure product sterility throughout the shelf-life or term of use of the drug product. Commonly used preservatives include benzyl alcohol, phenol and m-cresol. Although preservatives have a long history of use, the development of protein formulations that includes preservatives can be challenging. Preservatives almost always have a destabilizing effect (aggregation) on proteins, and this has become a major factor in limiting their use in multi-dose protein formulations (Roy et al. (2005), J. Pharm. Sci., 94 (2): 382-96). Benzyl alcohol has also been shown to affect protein structure and stability in a concentration-, temperature- and time-dependent manner. Due to these destabilizing effects, many lyophilized protein formulations are reconstituted with diluent containing benzyl alcohol to minimize the contact time with the protein prior to administration.

Most protein drugs have been formulated for single-use only. However, when multi-dose formulations are possible, they have the added advantage of enabling patient convenience, and increased marketability. A good example is that of human growth hormone (hGH) where the development of preserved formulations has led to commercialization of more convenient, multi-use injection pen presentations. At least four such pen devices containing preserved formulations of hGH are currently available. Norditropin® (liquid), Nutropin AQ® (liquid) & Genotropin (lyophilized-dual chamber cartridge) contain phenol while Somatrope® is formulated with m-cresol.

Several aspects need to be considered during the formulation development of preserved dosage forms. The effective preservative concentration in the drug product must be optimized. This requires testing a given preservative in the dosage form with concentration ranges that confer antimicrobial effectiveness without compromising protein stability. For example, three preservatives were successfully screened in the development of a liquid formulation for interleukin-1 receptor (Type I), using differential scanning calorimetry (DSC). The preservatives were rank-ordered based on their impact on stability at concentrations commonly used in marketed products (Remmele et al. (1998), Pharm. Res., 15 (2): 200-8).

As might be expected, development of liquid formulations containing preservatives are more challenging than lyophilized formulations. Freeze-dried products can be lyophilized without the preservative and reconstituted with a preservative containing diluent at the time of use. This shortens the time during which a preservative is in contact with the protein, thus significantly minimizing the associated stability risks. With liquid formulations, preservative effectiveness and stability have to be maintained over the entire product shelf-life (usually about 18-24 months). An important point to note is that preservative effectiveness has to be demonstrated in the final formulation containing the active drug and all excipient components.

Some preservatives can cause injection site reactions, which is another factor that needs consideration when choosing a preservative. In clinical trials that focused on the evaluation of preservatives and buffers in Norditropin®, pain perception was observed to be lower in formulations containing phenol and benzyl alcohol as compared to a formulation containing m-cresol (Kappelgaard (2004), Horm. Res. 62 Suppl 3:98-103). Interestingly, among the commonly used preservative, benzyl alcohol possesses anesthetic properties (Minogue and Sun (2005), Anesth. Analg. 100 (3): 683-6).

WORKING EXAMPLES

All publications, patents, and patent applications discussed and cited herein are hereby incorporated by reference in their entireties. It is understood that the disclosed invention is not limited to the particular methodology, protocols and materials described as these can vary. It is also understood that the terminology used herein is for the purposes of describing particular embodiments only and is not intended to limit the scope of the appended claims.

Those skilled in the art will recognize, or be able to ascertain using no more than routine experimentation, many equivalents to the specific embodiments of the invention described herein. Such equivalents are intended to be encompassed by the claims that follow.

Example 1

This experiment demonstrates that by adjusting fill weight targets, protein concentration can be precisely targeted for the respective reconstituted drug product.

Materials

Buffer containing: Mannitol, Sucrose, L-Histidine, Polysorbate 20 at pH 5

Container Vial, 3cc, Blowback, Type I Glass, Non-treated, 13 mm Finish with Stopper, 13 mm, 4432/50 V-50, romiplostim Filtered Purified Bulk Method
1. Dilute drug to target product formulation (0.5 mg/mL) utilizing required amount of the dilution buffer.
2. Filter formulated solution using a 0.22 μm Polyvinylidene difluoride (PVDF) filter.
3. Ensure vials and stopper: 3 cc vials have been washed and depyrogenated.
4. Fill sufficient quantity of vials to respective fill weight targets: 0.307, 0.322, 0.342, 0.357, 0.373 g.
5. Partially stopper vials and place in lyophilizer.
6. Run required lyophilization cycle with adequate freezing, vacuum, with primary and secondary drying, followed by stoppering and unloading of the lyophilized product in sealed vials.
7. Reconstitute product with set reconstitution volume of 0.32 mL of water for injection.
8. Measure resulting protein concentration in vials utilizing ultraviolet (UV) absorption. Absorbance is defined as the amount of light of a specific wavelength that is absorbed as it passes through an analyte. The Absorbance Unit is a function of the intrinsic absorbance of the molecule, its concentration and the path length of the analyte. Aromatic amino acids phenylalanine, tyrosine, and tryptophan in protein molecules absorb light in the UV range of 260-290 nm. UV absorption in this range is used routinely to measure protein presence in a solution.
9. Measure the osmolality of the product utilizing freezing point depression.
10. Perform analysis to determine effect of adjusted fill weight targets for both protein and osmolality.

TABLE 5

Summary of fill weights and protein concentration

| | Parameters | Experimental conditions | | | | |
|---|---|---|---|---|---|---|
| | | A | B | C | D | E |
| Input | Formulated bulk concentration (mg/mL) | 0.528 | 0.528 | 0.528 | 0.528 | 0.528 |
| | Average fill weight (g) | 0.307 | 0.322 | 0.342 | 0.357 | 0.373 |
| Output | Average protein concentration post-reconstitution (mg/mL) | 0.459 | 0.484 | 0.518 | 0.546 | 0.565 |

Figure 6:
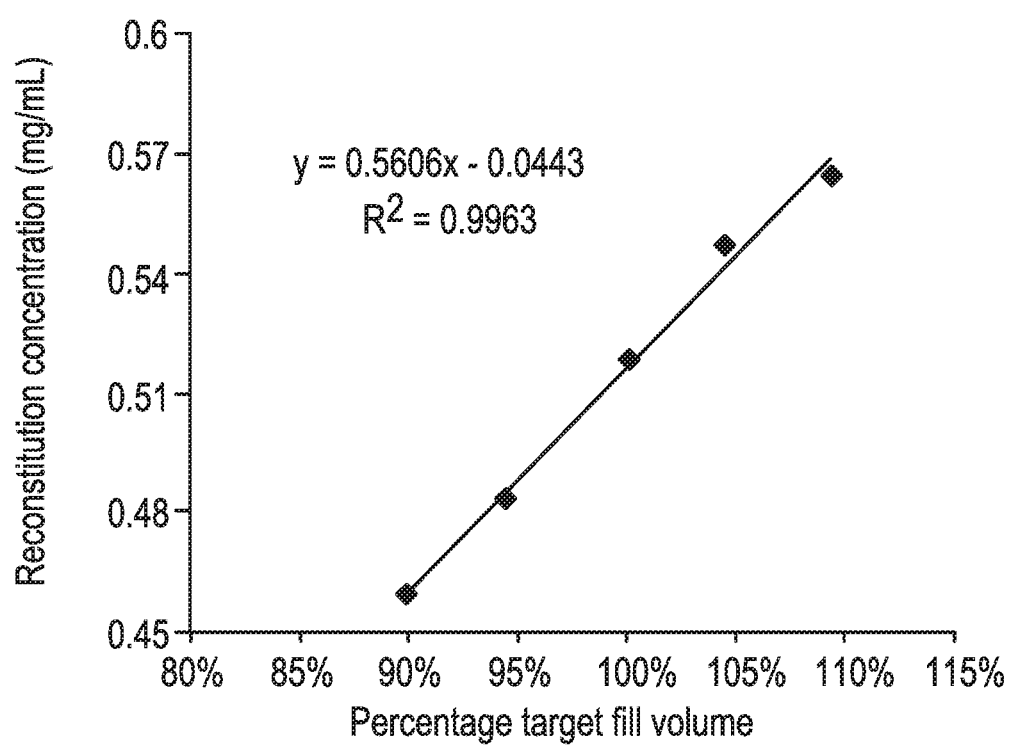
FIG. 6 shows normalized fill weights vs. product protein concentration post reconstitution as determined in accordance with Example 1 hereinafter.

A strong linear relationship between reconstituted protein concentration and fill volume was observed as evidenced by the $R^2$ of 0.9964 as shown in FIG. 6. This linear relationship can be explained theoretically based on protein mass balance, as shown below:

$$C_{reconstitution} * V_{reconstitution} = (C_{Formulated} - C_{loss}) * V_{fill} \quad \text{[Equation 1]}$$

$$C_{reconstitution} = \frac{C_{formulated} - C_{loss}}{V_{reconstitution}} * V_{fill} \quad \text{[Equation 2]}$$

Where $C_{reconstitution}$ is the protein concentration post-reconstitution, $V_{reconstitution}$ is the product volume post-reconstitution, $C_{formulated}$ is the formulated bulk protein concentration, $C_{loss}$ is the protein loss due to binding to filter and containers, and $V_{fill}$ is the fill volume in each vial. Since formulated bulk concentration, protein binding loss and reconstitution volume are constant in a given run, protein concentration post-reconstitution is proportional to fill volume as indicated in Equation 2.

In the pilot scale experiment, variability of final reconstituted drug product (DP) protein concentration was determined using 10 replicates at each filling condition, as shown in Table 6. Therefore, the observed variability represents both process and analytical variability, including the variability associated with reconstitution of the product.

TABLE 6

Protein concentration (reconstituted) variability under each filling condition

| | A (−10%) | B (−5%) | C (Target) | D (+5%) | E (+10%) |
|---|---|---|---|---|---|
| Number of replicates | 10 | 10 | 10 | 10 | 10 |
| Average (mg/mL) | 0.459 | 0.484 | 0.518 | 0.546 | 0.565 |
| Standard deviation (SD, mg/mL) | 0.0084 | 0.0133 | 0.0082 | 0.0052 | 0.0069 |
| Relative SD (%) | 1.83 | 2.76 | 1.58 | 0.94 | 1.23 |

Fill Weight Impact on Osmolality (Reconstituted DP)

The final drug product osmolality after reconstitution was tested for osmolality, for vials filled at five fill weight targets. The osmolality results before filling and post reconstitution are summarized in Table 7. The osmolality doesn't change post filling and reconstitution based on the results at the target fill weight of 0.341 grams, indicating that the excipients were not lost in appreciable amounts. Osmolality increases slightly at higher fill volumes, and decreases slightly at lower fill volumes when reconstitution volume is held constant.

TABLE 7

Summary of Fill weights and Osmolality

| | Parameters | A | B | C | D | E |
|---|---|---|---|---|---|---|
| Input | Formulated bulk osmolality (mOsm/kg)* | 312.4 | 312.4 | 312.4 | 312.4 | 312.4 |
| | Average fill weight (g) | 0.307 | 0.322 | 0.342 | 0.357 | 0.373 |
| | Average fill volume (mL) | 0.301 | 0.316 | 0.336 | 0.350 | 0.366 |
| | Normalized volume (%) | 89.9% | 94.3% | 100.2% | 104.6% | 109.3% |
| Output | Effective volume post reconstitution (mL) | 0.335 | 0.335 | 0.335 | 0.335 | 0.335 |
| | Average osmolality post reconstitution (mOsm/kg) | 280 | 294 | 313 | 327 | 342 |
| | Normalized osmolality (%) | 89.6% | 94.0% | 100.0% | 104.6% | 109.3% |

Figure 7:
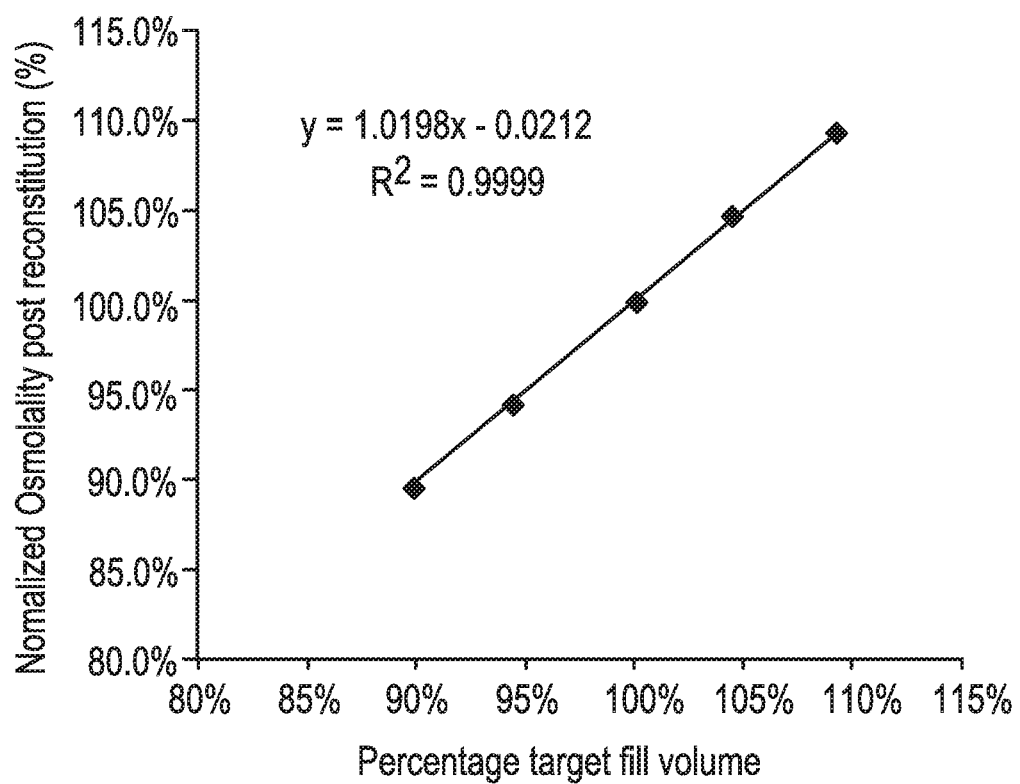
FIG. 7 shows normalized fill weights vs. osmolality as determined in accordance with Example 1 hereinafter.

A linear relationship was found if the fill weight/volume (normalized based on target of 0.341 g) is plotted versus the product osmolality (normalized based on target osmolality of 313 mOsm/kg at target fill weight), as shown in FIG. 7. This linear relationship can be explained by the definition of osmolality and its relationship with buffer component concentration.

Osmolality is a measure of solute concentration, defined as the number of osmoles (Osm) of solute per kilogram of solvent (osmol/kg or Osm/kg). Distinct from molarity (mole/L), osmolality measures moles of solute particles (such as dissociated ion) rather than moles of solute. Osmolality of a solution can be calculated from the following expression:

$$\text{Osmolality}(osm/kg) = \text{density} * \Sigma \varphi_i n_i C_i \quad \text{[Equation 3]}$$

Where $\varphi$ is the osmotic coefficient, n is the number of particles (e.g., ions) into which a molecule dissociates, and C is the molar concentration (mole/L) of the solute.

In the case when fill weight (or volume) is 10% higher than target volume, the concentration of each excipient species in the formulation is increased by 10% upon reconstitution to constant volume. Since $\varphi_i$ and $n_i$ are constant in a known formulation, 10% increase in concentration of each species results in 10% increase in osmolality as shown in Equation 3. Similarly, 10% decrease of fill volume results in 10% decrease in excipient concentration, and consequently 10% decrease in osmolality.

Example 2

The protein blinatumomab has 55 µg/mL formulated to 200 mM L-lysine-HCl, 25 mM citric acid, 15% (w/v) trehalose dihydrate, 0.1% (w/v) polysorbate 80, pH 7.0. The formulated protein allowable range is measured at the filtered bulk stage. Bulk concentrations ranging from 48.0 µg/mL to 65.0 µg/mL are used. Target fill weights are calculated based upon the measured protein concentration to target a reconstituted drug product of 12.5 mcg/mL when reconstituted with 3 mL of water.

$$C_{reconstitution} * V_{reconstitution} = (C_{Formulated} - C_{loss}) * V_{fill}$$

Where $$C_{reconstitution} * V_{reconstitution} = \text{Target protein content}_{reconstitution}$$

Then the Target protein content can then be multiplied by the product density and divided by the measured drug concentration (adjusted for loss due to binding if needed) to determine the Target fill weight.

The target fill weight is calculated according to the following formula, with a corresponding fill weight range of 0.634 to 0.858 gm.

$$\text{Fill weight(g)} = \frac{\text{target dose}\left(38.5\ \mu\frac{g}{vial}\right) \times \text{density}\left(1.07\frac{g}{mL}\right)}{DS\ \text{concentration}\left(x\ \mu\frac{g}{mL}\right)}$$

wherein DS is generally understood by persons of ordinary skill in the art to refer to drug substance. Stated more generally, $$\text{adjusted fill weight} = \frac{(\text{target fixed dose of the therapeutic protein}) \times (\text{density})}{\text{therapeutic protein concentration in bulk formulation.}}$$

Example 3

Infliximab drug product has 20±1.5 mg/mL infliximab, formulated with 10 mM sodium phosphate, 10% (w/v) sucrose, 0.01% (w/v) polysorbate 80, pH 7.2 post reconstitution with 10 mL Water for Injection.

The target fill weight is calculated according to following formula, with a corresponding fill weight range of 4.85 to 5.63 gm.

Calculation of Target Fill Weight $$\text{Target fill weight(g)} = \frac{(\text{Target protein content}(100\ mg)) \times \left(\text{Density}\left(1.042\frac{g}{mL}\right)\right)}{\text{Released drug substance protein concentration}\left(\frac{mg}{mL}\right)}$$

Example 4

Trastuzumab has 21 mg/mL formulated with, 0.303 mg/mL L-Histidine, 0.470 mg/mL L-Histidine Hydrochloride Monohydrate, 19.1 mg/mL α,α-Trehalose Dihydrate, 0.0840 mg/mL Polysorbate 20, at pH 6.1. The target fill weight is calculated according to formula below, with varying fill weight ranges based upon the product delivery requirements. The fill weight targets range from 3.1 to 21.2 gm (depending upon the respective presentation). This product has multiple presentations with a pooled drug substance concentration of 21 mg/mL.

The target fill weight for each drug product lot for this Example 4 and the subsequent examples is calculated using the following information:

$$\text{Target fill weight[g]} = \frac{(\text{Target protein content[mg]}) \times (\text{Density[g/mL]})}{\text{Pooled drug substance concentration[mg/mL]}}$$

As an example, the target fill weight for a 150 mg presentation[g] =

$$\frac{(156\ mg) \times (1.01\ g/mL)}{\text{Pooled drug substance concentration[21 mg/mL]}}$$

As another example, the target fill weight for a 420 mg presentation[g] =

$$\frac{(440\ mg) \times (1.01\ g/mL)}{\text{Pooled drug substance concentration[21 mg/mL]}}$$

As a further example the target fill weight for a 60 mg presentation[g] =

$$\frac{(65\ mg) \times (1.01\ g/mL)}{\text{Pooled drug substance concentration[21 mg/mL]}}$$

Example 5

AMG 701 is a single chain, variable domain Bi-specific T-cell Engager (BiTE®) anti-BCMA/anti-CD3 antibody construct (see NCI Drug Dictionary and other references). AMG 701 with protein concentration at 1 mg/mL was formulated with 10 mM L-glutamic acid, 9.0% (w/v) sucrose, 0.010% (w/v) polysorbate 80, at pH 4.2. The target fill weight is calculated according to formula below, with varying fill weight ranges based upon the product delivery requirements. AMG 701 has three presentations, with the fill weight targets range for the first presentation from 0.47 to 0.57 gm., the second presentation from 1.60 to 1.96 gm, and the third presentation from 3.28 to 4.01 gm.

For the first presentation:

$$\text{Target fill weight(g)} = \frac{(\text{Target protein content}(0.50 \text{ mg})) \times \left(\text{Density}\left(1.032 \frac{g}{mL}\right)\right)}{\text{Released drug substance protein concentration}\left(1.0 \frac{mg}{mL}\right)}$$

For the second presentation:

$$\text{Target fill weight(g)} = \frac{(\text{Target protein content}(1.71 \text{ mg})) \times \left(\text{Density}\left(1.032 \frac{g}{mL}\right)\right)}{\text{Released drug substance protein concentration}\left(1.0 \frac{mg}{mL}\right)}$$

For the third presentation:

$$\text{Target fill weight(g)} = \frac{(\text{Target protein content}(3.5 \text{ mg})) \times \left(\text{Density}\left(1.032 \frac{g}{mL}\right)\right)}{\text{Released drug substance protein concentration}\left(1.0 \frac{mg}{mL}\right)}$$

Example 6

AMG 330 is an anti-CD33/anti-CD3 single chain, variable domain Bi-specific T-cell Engager (BiTE®) (see NCI Drug Dictionary and other references). AMG 300 with protein concentration at 0.5 mg/mL was formulated with 10 mM potassium phosphate, 8.0% (w/v) sucrose, 1.0% (w/v) sulfobutylether betacyclodextrin (SBE-CD), 0.010% (w/v) polysorbate 80 at pH 6.1. The target fill weight is calculated according to formula below, with varying fill weight ranges based upon the product delivery requirements. The fill weight targets range from 1.2 to 1.5 gm. The target fill weight is calculated as follows:

$$\text{Target fill weight(g)} = \frac{(\text{Target protein content}(0.64 \text{ mg})) \times \left(\text{Density}\left(1.033 \frac{g}{mL}\right)\right)}{\text{Drug substance protein concentration}\left(0.5 \frac{mg}{mL}\right)}$$

In general, the methodology can be used in the case where a target amount of product is required in the container to ensure that the product post-reconstitution is at the required concentration. This result is achieved by determining the amount of volume of the reconstituted product; for example, 1 mL volume with a desired concentration of 1 mg/mL of therapeutic protein, leading to a total amount of required protein content of 1 mg.

$$\text{Target protein content}[mg] = (\text{Protein concentration }[mg/mL] \times \text{Reconstituted volume}[mL])$$

The target protein content is then used to calculate the target fill weight based upon the formula below. The in-process or measured drug concentration is typically measured as part of the formulation process to compensate for any process variability. In some cases, an adjustment to the target protein content is made to compensate for loss of product due to binding. Confidence in the measured drug concentration is required to ensure precise targeting of the fill weights.

$$\text{Target fill weight}[g] = \frac{(\text{Target protein content}[mg]) \times (\text{Density}[g/mL])}{\text{Measured drug concentration}[mg/mL]}$$

This is a specific example as the therapeutic product both for the in-process concentration and the reconstituted product can range from micrograms (mcg or µg) per milliliter (mL) to milligrams (mg) per milliliter (mL).

Verification of osmolality is required, as discussed above (based upon experimental findings). Limitations on the allowed measured drug concentration are established in combination with the fill weight targets to achieve the required amount of active drug filled into the container to provide assurance that the reconstituted product meets both the product (active drug or protein) concentration as well as the osmolality specification limits.

All publications, patents, and patent applications discussed and cited herein are hereby incorporated by reference in their entireties. It is understood that the disclosed invention is not limited to the particular methodology, protocols and materials described as these can vary. It is also understood that the terminology used herein is for the purposes of describing particular embodiments only and is not intended to limit the scope of the appended claims.

Those skilled in the art will recognize or be able to ascertain using no more than routine experimentation many equivalents to the specific embodiments of the invention described herein. Such equivalents are intended to be encompassed by the claims that follow.

What is claimed is:

1. A process for making a lyophilized pharmaceutical formulation of a therapeutic protein, which comprises:

a. providing a formulation of a bulk amount of the therapeutic protein,
b. measuring the concentration of the therapeutic protein in said bulk formulation,
c. determining a fill weight of the bulk formulation according to the following formula to achieve a target fixed dose of the therapeutic protein in a container, $$\text{fill weight} = \frac{(\text{target fixed dose of the therapeutic protein}) \times (\text{density of bulk formulation})}{\text{therapeutic protein concentration in bulk formulation.}}$$

and
d. lyophilizing the formulation in the container.

2. The process of claim 1, wherein the process further comprises reconstituting the lyophilized formulation, wherein the concentration of the therapeutic protein in the reconstituted formulation is less than or equal to about 20 mg/mL.

3. The process of claim 1, wherein the therapeutic protein is selected from romiplostim, blinatumomab, infliximab, trastuzumab, AMG 701, and AMG 330.

4. The process of claim 2, wherein the therapeutic protein is romiplostim and the concentration of romiplostim is about 0.5 mg/mL.

5. The process of claim 2, wherein the reconstituted formulation comprises about 0.5 mg/mL romiplostim, about 10 mM histidine, about 4% w/v mannitol, about 2% w/v sucrose and about 0.004% polysorbate 20, and has a pH of about pH 5.0.

6. The process of claim 1, wherein the therapeutic protein is blinatumomab and the therapeutic protein concentration in the final formulation is about 55 µg/mL.

7. The process of claim 1, wherein the formulation comprises about 55 µg/mL blinatumomab in about 25 mM citric acid monohydrate, about 15% (w/v) trehalose, about 200 mM L-lysine hydrochloride, and about 0.1% (w/v) polysorbate 80 at about pH 7.0.

8. The process of claim 1, wherein the therapeutic protein is infliximab and the therapeutic protein concentration in the final formulation is about 20±1.5 mg/mL.

9. The process of claim 1, wherein the final formulation comprises about 20±1.5 mg/mL infliximab, about 10 mM sodium phosphate, about 10% (w/v) sucrose, and about 0.01% (w/v) polysorbate 80 at about pH 7.2.

10. The process of claim 1, wherein the therapeutic protein is trastuzumab and the therapeutic protein concentration in the final formulation is about 21 mg/mL.

11. The process of claim 1, wherein the final formulation comprises about 21 mg/mL trastuzumab, about 0.303 mg/mL L-histidine, about 0.470 mg/mL L-histidine hydrochloride monohydrate, about 19.1 mg/mL a,a-trehalose dihydrate, and about 0.0840 mg/mL polysorbate 20 at about pH 6.1.

12. The process of claim 1, wherein the therapeutic protein is AMG 701 and the therapeutic protein concentration in the final formulation is about 1 mg/mL.

13. The process of claim 1, wherein the final formulation comprises about 1 mg/ml AMG 701, about 10 mM L-glutamic acid, about 9.0% (w/v) sucrose, and about 0.010% (w/v) polysorbate 80 at about pH 4.2.

14. The process of claim 1, wherein the therapeutic protein is AMG 330 and the therapeutic protein concentration in the final formulation is about 0.5 mg/mL.

15. The process of claim 1, wherein the final formulation comprises about 0.5 mg/mL AMG 330, about 10 mM potassium phosphate, about 8.0% (w/v) sucrose, about 1.0% (w/v) sulfobutylether betacyclodextrin (SBE-CD), and about 0.010% (w/v) polysorbate 80 at about pH 6.1.

16. The process of claim 1, wherein the therapeutic protein concentration in the bulk formulation is less than or equal to about 25 mg/mL.

17. The process of claim 1, wherein the therapeutic protein is a bispecific single chain antibody construct.

18. The process of claim 1, wherein the therapeutic protein is selected from AMG 701 and AMG 330.

19. The process of claim 1, wherein the container is a stock keeping unit (SKU).

20. A lyophilized pharmaceutical formulation prepared according to the process of claim 1.

21. The process of claim 2 or claim 16, wherein the reconstituting comprises using water for injection.

22. The process of claim 4 or 5, wherein the reconstituted formulation is suitable for subcutaneous administration.

* * * * *